United States Patent
Koyanagi et al.

(10) Patent No.: US 10,283,719 B2
(45) Date of Patent: May 7, 2019

(54) ORGANIC THIN-FILM TRANSISTOR AND METHOD FOR MANUFACTURING THE SAME, MATERIAL FOR ORGANIC THIN-FILM TRANSISTOR, COMPOSITION FOR ORGANIC THIN-FILM TRANSISTOR, COMPOUND, AND ORGANIC SEMICONDUCTOR FILM

(71) Applicants: FUJIFILM Corporation, Tokyo (JP); THE UNIVERSITY OF TOKYO, Tokyo (JP)

(72) Inventors: Masashi Koyanagi, Kanagawa (JP); Hiroaki Tsuyama, Kanagawa (JP); Eiji Fukuzaki, Kanagawa (JP); Yoshihisa Usami, Kanagawa (JP); Tetsuya Watanabe, Kanagawa (JP); Takashi Goto, Kanagawa (JP); Toshihiro Okamoto, Tokyo (JP); Junichi Takeya, Tokyo (JP)

(73) Assignees: FUJIFILM Corporation, Tokyo (JP); THE UNIVERSITY OF TOKYO, Tokyo (JP)

( * ) Notice: Subject to any disclaimer, the term of this patent is extended or adjusted under 35 U.S.C. 154(b) by 0 days.

(21) Appl. No.: 15/884,512

(22) Filed: Jan. 31, 2018

(65) Prior Publication Data
US 2018/0159048 A1  Jun. 7, 2018

Related U.S. Application Data

(63) Continuation of application No. PCT/JP2016/072648, filed on Aug. 2, 2016.

(30) Foreign Application Priority Data

Aug. 4, 2015 (JP) ................. 2015-154613
Aug. 1, 2016 (JP) ................. 2016-151058

(51) Int. Cl.
  *C07D 517/04*  (2006.01)
  *H01L 51/00*  (2006.01)
  *H01L 29/786*  (2006.01)
  *H01L 51/05*  (2006.01)
  *C09B 57/00*  (2006.01)
  *C09B 69/00*  (2006.01)

(52) U.S. Cl.
  CPC ........ *H01L 51/0071* (2013.01); *C07D 517/04* (2013.01); *C09B 57/00* (2013.01); *C09B 69/008* (2013.01); *H01L 29/786* (2013.01); *H01L 51/0068* (2013.01); *H01L 51/05* (2013.01); *H01L 51/0003* (2013.01); *H01L 51/0005* (2013.01); *H01L 51/0545* (2013.01); *H01L 51/0558* (2013.01)

(58) Field of Classification Search
  CPC .. C07D 517/04; C07D 513/02; C07D 498/02; C07D 487/02; H01L 21/67; H01L 51/0071
  USPC ........... 540/16; 313/499, 498; 548/148, 217, 548/301.7; 556/9
  See application file for complete search history.

(56) References Cited

FOREIGN PATENT DOCUMENTS

| JP | 2013-207085 A | 10/2013 |
|---|---|---|
| JP | 2014-078729 A | 5/2014 |
| JP | 2014-209597 A | 11/2014 |
| JP | 2015-502937 A | 1/2015 |
| JP | 2015-122437 A | 7/2015 |
| WO | 2010/024388 A1 | 3/2010 |
| WO | 2013/078407 A1 | 5/2013 |
| WO | 2014/148614 A1 | 9/2014 |
| WO | 2014/175351 A1 | 10/2014 |
| WO | 2015/016344 A1 | 2/2015 |

OTHER PUBLICATIONS

The extended European search report issued by the European Patent Office dated Mar. 27, 2018, which corresponds to European Patent Application No. 16833037.1-1110 and is related to U.S. Appl. No. 15/884,512.
International Search Report issued in PCT/JP2016/072648; dated Oct. 4, 2016.
Written Opinion issued in PCT/JP2016/072648; dated Oct. 4, 2016.
Holliday et al.; Advances in Charge Carrier Mobilities of Semiconducting Polymers Used in Organic Transistors; Chemistry of Materials; 2014; pp. 647-663; vol. 26.

*Primary Examiner* — Charanjit Aulakh
(74) *Attorney, Agent, or Firm* — Studebaker & Brackett PC

(57) ABSTRACT

An object of the present invention is to provide a compound which, when used for organic semiconductor films in organic thin-film transistors, makes the organic thin-film transistors exhibit a high carrier mobility, a material for an organic thin-film transistor for which the compound is used, a composition for an organic thin-film transistor, an organic thin-film transistor and a method for manufacturing the same, and an organic semiconductor film.
An organic thin-film transistor of the present invention contains a compound represented by General Formula (1) in an organic semiconductor film (organic semiconductor layer) thereof.

General Formula (1)

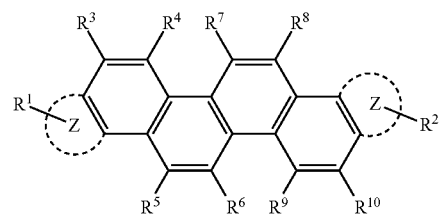

22 Claims, 3 Drawing Sheets

ORGANIC THIN-FILM TRANSISTOR AND METHOD FOR MANUFACTURING THE SAME, MATERIAL FOR ORGANIC THIN-FILM TRANSISTOR, COMPOSITION FOR ORGANIC THIN-FILM TRANSISTOR, COMPOUND, AND ORGANIC SEMICONDUCTOR FILM

CROSS-REFERENCE TO RELATED APPLICATIONS

This application is a Continuation of PCT International Application No. PCT/JP2016/072648 filed on Aug. 2, 2016, which claims priority under 35 U.S.C. § 119(a) to Japanese Patent Application No. 2015-154613 filed on Aug. 4, 2015 and Japanese Patent Application No. 2016-151058 filed on Aug. 1, 2016. Each of the above applications is hereby expressly incorporated by reference, in its entirety, into the present application.

BACKGROUND OF THE INVENTION

1. Field of the Invention

The present invention relates to an organic thin-film transistor and a method for manufacturing the same, a material for an organic thin-film transistor, a composition for an organic thin-film transistor, a compound, an organic semiconductor film, and the like.

2. Description of the Related Art

Organic thin-film transistors (organic TFT) having organic semiconductor films (organic semiconductor layers) are used in field-effect transistors (FET) that are used in liquid crystal displays or organic electroluminescence (EL) displays, apparatuses in which logic circuits are used such as radio frequency identifier (RFID: RF tag) or memories, or the like since weight reduction, cost reduction, and softening are possible.

It is known that, as compounds for forming the above-described organic semiconductor films, polycondensed compounds including heteroaromatic rings are useful.

For example, WO2010/024388A discloses a compound in which a n conjugation of the compound is enlarged by further condensing a heteroaromatic ring (as a heteroaromatic ring group, furan, thiophene, or N-substituted pyrrole) into a chrysene skeleton.

SUMMARY OF THE INVENTION

Meanwhile, in recent years, from the viewpoint of improving the performance of organic thin-film transistors, there has been a current demand for the additional improvement of the carrier mobility of organic thin-film transistors.

In response to such a demand, the present inventors carried out additional studies regarding organic thin-film transistors for which a polycondensed compound obtained by further condensing a heteroaromatic ring (furan, thiophene, or N-substituted pyrrol as a heteroaromatic ring group) into a chrysene skeleton as disclosed in WO2010/024388A is used, and found that there is a room for the additional improvement of the carrier mobility.

Therefore, an object of the present invention is to provide a compound which, when used for organic semiconductor films in organic thin-film transistors, makes the organic thin-film transistors exhibit a high carrier mobility, a material for an organic thin-film transistor for which the compound is used, a composition for an organic thin-film transistor, an organic thin-film transistor and a method for manufacturing the same, and an organic semiconductor film.

As a result of intensive studies regarding the above-described object, the present inventors found that the use of a compound represented by General Formula (1) enables the obtainment of desired effects and completed the present invention.

That is, the present inventors found that the object can be achieved by the following constitutions.

<1> An organic thin-film transistor comprising: an organic semiconductor film including a compound which is represented by General Formula (1) and has a molecular weight of 3,000 or less.

<2> The organic thin-film transistor according to <1>, in which, in General Formula (1), the number of carbon atoms included in each of $R^1$ to $R^{10}$ is independently 30 or less.

<3> The organic thin-film transistor according to <1> or <2>, in which, in General Formula (1), at least one of $R^1, \ldots,$ or $R^{10}$ has, as $R^W$, any group selected from the group consisting of an alkyl group having 20 or less carbon atoms, an aryl group having 20 or less carbon atoms, and a heteroaryl group having 20 or less carbon atoms, all of which may have a substituent.

<4> The organic thin-film transistor according to any one of <1> to <3>, in which, in General Formula (1), $R^1$ and $R^2$ are the same group, $R^3$ and $R^{10}$ are the same group, $R^4$ and $R^9$ are the same group, $R^5$ and $R^8$ are the same group, and $R^6$ and $R^7$ are the same group.

<5> The organic thin-film transistor according to any one of <1> to <4>, in which the compound is represented by General Formula (2) or General Formula (3).

<6> The organic thin-film transistor according to any one of <1> to <5>, in which the compound is represented by General Formula (4) or General Formula (5).

<7> The organic thin-film transistor according to any one of <1> to <6>, in which the compound is represented by General Formula (6) or General Formula (7).

<8> The organic thin-film transistor according to <7>, in which, in General Formula (6) or (7), $L^W$ is a single bond.

<9> The organic thin-film transistor according to <7> or <8>, in which, in General Formula (6) or (7), both $R^1$ and $R^2$ include an aliphatic hydrocarbon group having 20 or less carbon atoms.

<10> A compound which is represented by General Formula (1) and has a molecular weight of 3,000 or less.

<11> The compound according to <10>, in which, in General Formula (1), the number of carbon atoms included in each of $R^1$ to $R^{10}$ is independently 30 or less.

<12> The compound according to <10> or <11>, in which, in General Formula (1), at least one of $R^1, \ldots,$ or $R^{10}$ has, as $R^W$, any group selected from the group consisting of an alkyl group having 20 or less carbon atoms, an aryl group having 20 or less carbon atoms, and a heteroaryl group having 20 or less carbon atoms, all of which may have a substituent.

<13> The compound according to any one of <10> to <12>, in which, in General Formula (1), $R^1$ and $R^2$ are the same group, $R^3$ and $R^{10}$ are the same group, $R^4$ and $R^9$ are the same group, $R^5$ and $R^8$ are the same group, and $R^6$ and $R^7$ are the same group.

<14> The compound according to any one of <10> to <13>, in which the compound is represented by General Formula (2) or General Formula (3).

<15> The compound according to any one of <10> to <14>, in which the compound is represented by General Formula (4) or General Formula (5).

<16> The compound according to any one of <10> to <15>, in which the compound is represented by General Formula (6) or General Formula (7).

<17> The compound according to <16>, in which, in General Formula (6) or (7), $L^W$ is a single bond.

<18> The compound according to <17>, in which, in General Formula (6) or (7), both $R^1$ and $R^2$ include an aliphatic hydrocarbon group having 20 or less carbon atoms.

<19> A material for an organic thin-film transistor comprising: the compound according to any one of <10> to <18>.

<20> A composition for an organic thin-film transistor comprising: the compound according to any one of <10> to <18>.

<21> A method for manufacturing an organic thin-film transistor comprising: a step of forming an organic semiconductor film by applying the composition for an organic thin-film transistor according to <20> on a substrate and drying the composition.

<22> An organic semiconductor film comprising: the compound according to any one of <10> to <18>.

In the present specification, the expression of a compound is used to refer to the compound, and, additionally, a salt thereof and an ion thereof.

In the present specification, in a case in which a plurality of substituents, linking groups, or the like (hereinafter, referred to as substituents or the like) is indicated by a specific reference sign or a plurality of substituents or the like is specified at the same time, the respective substituents or the like may be identical to or different from one another. This is also true in the case of specifying the number of substituents or the like.

In addition, unless particularly otherwise described, in a case in which a plurality of substituents or the like comes close to one another (particularly, is adjacent to one another), the substituents or the like may be linked or condensed to one another and thus form a ring.

Furthermore, in the present specification, substituents or the like that are not clarified as being substituted or non-substituted may further have a substituent therein unless intended effects are not impaired. This is also true for compounds that are not clarified as being substituted or nonsubstituted.

In the present specification, numerical ranges expressed using "to" include numerical values before and after "to" as the lower limit value and the upper limit value.

According to the present invention, it is possible to provide a compound which, when used for organic semiconductor films in organic thin-film transistors, makes the organic thin-film transistors exhibit a high carrier mobility, a material for an organic thin-film transistor for which the compound is used, a composition for an organic thin-film transistor, an organic thin-film transistor and a method for manufacturing the same, and an organic semiconductor film.

DESCRIPTION OF THE PREFERRED EMBODIMENTS

[Organic Thin-Film Transistor]

Figure 1:
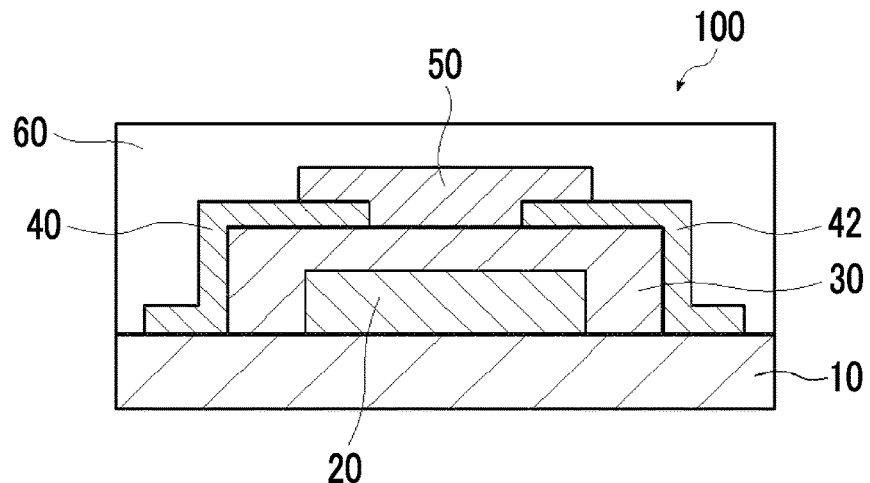
FIG. 1 is a schematic cross-sectional view of a bottom contact-type organic thin-film transistor according to an embodiment of the present invention.

An organic thin-film transistor of the present invention includes a compound which is represented by General Formula (1) and has a molecular weight of 3,000 or less in an organic semiconductor film (organic semiconductor layer) thereof.

The compound represented by General Formula (1) has a characteristic that, in organic semiconductor films formed of fine crystal thin films, the phases of the electron orbitals of molecules in fine crystals favorably match, the interaction among the respective molecules is strong, and the molecules are tightly packed, and thus the highest occupied molecular orbitals (HOMO) of the molecules are likely to overlap one another.

That is, it is considered that, in structures in which a chrysene skeleton is further condensed with a heteroaromatic ring as represented by General Formula (1), in a case in which a heteroaromatic ring included in a molecule (corresponding to Z in General Formula (1)) is turned into selenophene, thiazole, oxazole, imidazole, or silole, compared with compounds condensed with furan, thiophene, or N-substituted pyrrole as exemplified in WO2010/024388A of the related art, the interaction among molecules is far stronger, and the HOMO's of the molecules are more likely to overlap one another. As a result, the compound has a higher carrier mobility than the compound described in WO2010/024388A. Particularly, a selenium atom has a large orbital coefficient, and thus, in the present skeleton, in a case in which the heteroaromatic ring included in the molecule (corresponding to Z in General Formula (1)) is turned into selenophene, the HOMO's of the molecules are far more likely to overlap one another, and an amazingly excellent carrier mobility develops.

In addition, in a case in which the heteroaromatic ring included in the molecule (corresponding to Z in General Formula (1)) is turned into selenophene or silole (particularly, selenophene), a plurality of kinds of structural isomers having hetero atoms in different locations exists. Among them, in the compound represented by General Formula (1X), compared with other structural isomers, it is considered that the interaction among molecules is stronger and the HOMO's of the molecules are more likely to overlap one another, and an excellent carrier mobility can be obtained regardless of film-forming means such as coating or deposition and transistor layer constitutions.

General Formula (1X)

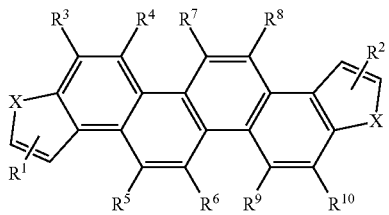

(In General Formula (1X), X represents a Se atom or a Si atom, and $R^1$ to $R^{10}$ each are the same as $R^1$ to $R^{10}$ in General Formula (1).)

<Compound Represented by General Formula (1)>

The compound represented by General Formula (1) is included in the organic semiconductor film (organic semiconductor layer) of the organic thin-film transistor.

The compound represented by General Formula (1) is a new compound and can not only be preferably used in the organic semiconductor film of the organic thin-film transistor but also be used in other uses described below.

General Formula (1)

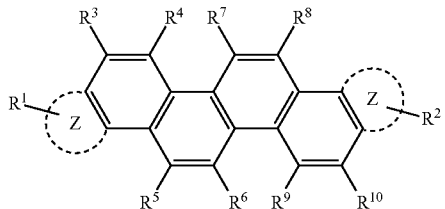

Z represents a heteroaromatic ring of a 5-membered ring selected from the group consisting of selenophene, thiazole, oxazole, imidazole, and silole, and $R^1$ to $R^{10}$ each independently represent a group represented by Formula (W).

In Formula (W), $L^W$ is a divalent linking group of any of a single bond, —O—, —S—, —$NR^{11}$—, —CO—, —SO—, —$SO_2$—, or —$Si(R^{12})(R^{13})$— or a divalent linking group obtained by bonding two or more divalent linking groups described above, and $R^W$ represents a hydrogen atom, a halogen atom, or an alkyl group, an alkenyl group, an alkynyl group, an aryl group, or a heteroaryl group, all of which may have a substituent.

$R^{11}$ to $R^{13}$ represent a hydrogen atom or an alkyl group, an alkenyl group, an alkynyl group, an aryl group, or a heteroaryl group, all of which may have a substituent.

Meanwhile, in the present specification, unless particularly otherwise described, "alkyl groups" and "alkenyl groups" refer to all of linear, branched, and cyclic alkyl groups and all of linear, branched, and cyclic alkenyl groups. Meanwhile, examples of cyclic alkyl groups include a cycloalkyl group, a bicycloalkyl group, a tricycloalkyl group, and the like. In addition, examples of cyclic alkenyl groups include a cycloalkenyl group, a bicycloalkenyl group, and the like.

In addition, in the present specification, examples of hetero atoms included in "heteroaryl groups" include a sulfur atom (S), an oxygen atom (O), a nitrogen atom (N), and the like.

The molecular weight of the compound represented by General Formula (1) is 3,000 or less, preferably 250 to 2,000, more preferably 300 to 1,000, and still more preferably 350 to 800. The molecular weight is preferably set in the above-described range since it is possible to further increase the solubility in solvents.

In General Formula (1), Z represents a heteroaromatic ring of a 5-membered ring selected from the group consisting of selenophene, thiazole, oxazole, imidazole, and silole.

In a case in which Z is selenophene or silole, a plurality of structural isomers exists, and, from the viewpoint of improving the carrier mobility, the hetero atom is preferably present in a location represented by General Formula (1X).

Z is preferably selenophene or thiazole and particularly preferably selenophene as in General Formulae (2) to (7) described below.

In General Formula (1), $R^1$ to $R^{10}$ each independently represent a group represented by Formula (W).

$L^W$ is a divalent linking group of any of a single bond, —O—, —S—, —$NR^{11}$—, —CO—, —SO—, —$SO_2$—, or —$Si(R^{12})(R^{13})$— or a divalent linking group obtained by bonding two or more divalent linking groups described above, preferably a single bond, —O—, —S—, —$NR^{11}$—, —CO—, —O—CO—, —CO—O—, —$NR^{11}$—CO—, —CO—$NR^{11}$—, —O—CO—O—, —$NR^{11}$—CO—O—, —OCO—$NR^{11}$— or —$NR^{11}$—CO—$NR^{11}$—, more preferably a single bond, —O—, —S—, —$NR^{11}$—, —CO—, —O—CO—, or —CO—O—, and still more preferably a single bond.

$R^{11}$ to $R^{13}$ represent a hydrogen atom or an alkyl group (preferably having 1 to 20 carbon atoms), an alkenyl group (preferably having 2 to 6 carbon atoms), an alkynyl group (preferably having 2 to 6 carbon atoms), an aryl group (preferably having 6 to 14 carbon atoms), or a heteroaryl group (preferably having 3 to 12 carbon atoms), all of which may have a substituent and is preferably a hydrogen atom, an alkyl group, or an aryl group, more preferably a hydrogen atom or an alkyl group, and still more preferably an alkyl group having 1 to 8 carbon atoms.

$R^W$ represents a hydrogen atom, a halogen atom, or an alkyl group, an alkenyl group, an alkynyl group, an aryl group, or a heteroaryl group, all of which may have a substituent.

The alkyl group is preferably an alkyl group having 1 to 20 carbon atoms, more preferably an alkyl group having 2 to 15 carbon atoms, and still more preferably an alkyl group having 3 to 10 carbon atoms. The alkyl group is preferably a linear alkyl group.

The alkenyl group is preferably an alkenyl group having 2 to 6 carbon atoms, more preferably an alkenyl group having 2 to 4 carbon atoms, and still more preferably an alkenyl group having 2 carbon atoms.

The alkynyl group is preferably an alkynyl group having 2 to 6 carbon atoms, more preferably an alkynyl group having 2 to 4 carbon atoms, and still more preferably an alkynyl group having 2 carbon atoms.

The aryl group is preferably an aryl group having 6 to 20 carbon atoms, more preferably an aryl group having 6 to 14 carbon atoms, and still more preferably an aryl group having 6 to 10 carbon atoms.

The heteroaryl group is preferably a heteroaryl group having 3 to 20 carbon atoms, more preferably a heteroaryl group having 3 to 12 carbon atoms, and still more preferably an heteroaryl group having 3 to 8 carbon atoms.

In General Formula (1), among $R^1$ to $R^{10}$, from the viewpoint of the crystal structure and the intermolecular interaction, at least one group preferably has a group other than a hydrogen atom (hereinafter, referred to as "substituent W"), and the number of the substituents W is more preferably 2 to 4 and particularly preferably 2.

In a case in which General Formula (1) has the substituents W, from the viewpoint of the intermolecular interaction and the solubility, the number of carbon atoms in the substituent W is preferably 30 or less, more preferably 25 or less, still more preferably 20 or less, and particularly preferably 16 or less. In other words, in a case in which General Formula (1) has the substituents W, the number of carbon atoms included in each of $R^1$ to $R^{10}$ (the total number of carbon atoms included in both $L^W$ and $R^W$ in Formula (W)) is preferably in the above-described numerical range independently.

In General Formula (1), in a case in which the substituents W are introduced into $R^1$ to $R^{10}$, the substituents W are preferably disposed at locations so that the entire molecule forms a point symmetric structure, and the substituents of the same kind are preferably disposed at locations in which the entire molecule forms a point symmetric structure so that the entire molecule, including the structure of the substituents, forms a point symmetric structure. Specifically, a case in which the substituents W (preferably substituents of the same kind) are present at the locations of both $R^1$ and $R^2$, a case in which the substituents W (preferably substituents of the same kind) are present at the locations of both $R^3$ and $R^{10}$, a case in which the substituents W (preferably substituents of the same kind) are present at the locations of both $R^4$ and $R^9$, a case in which the substituents W (preferably substituents of the same kind) are present at the locations of both $R^5$ and $R^8$, a case in which the substituents W (preferably substituents of the same kind) are present at the locations of both $R^6$ and $R^7$, and combinations of two or more cases described above are preferred. Among these, from the viewpoint of the crystal structure and the intermolecular interaction, the case in which the substituents W are present at the locations of both $R^1$ and $R^2$ is more preferred.

In General Formula (1), from the viewpoint of the intermolecular interaction and the solubility, at least one of $R^1, \ldots,$ or $R^{10}$ preferably has, as $R^W$, any group selected from the group consisting of an alkyl group having 20 or less carbon atoms (preferably 1 to 20 carbon atoms), an aryl group having 20 or less carbon atoms (preferably 6 to 20 carbon atoms), and a heteroaryl group having 20 or less carbon atoms (preferably 3 to 20 carbon atoms), in at least one of the combinations of $R^1$ and $R^2$, $R^3$ and $R^{10}$, $R^4$ and $R^9$, $R^5$ and $R^8$, and $R^6$ and $R^7$, the groups each more preferably have the above-described groups independently, and both $R^1$ and $R^2$ each still more preferably have the above-described groups independently.

In General Formula (1), from the viewpoint of the intermolecular interaction and the solubility, it is preferable that at least one of $R^1, \ldots,$ or $R^{10}$ includes an aliphatic hydrocarbon group having 20 or less carbon atoms, and it is more preferable that $R^1$ and $R^2$ include an aliphatic hydrocarbon group having 20 or less carbon atoms. For example, in a case in which $R^1$ and $R^2$ has, as $R^W$, an alkyl group having 20 or less carbon atoms (preferably having 1 to 20 carbon atoms) as described above, the alkyl group having 20 or less carbon atoms (preferably having 1 to 20 carbon atoms) corresponds to an aliphatic hydrocarbon group, meanwhile, for example, in a case in which $R^1$ and $R^2$ has, as $R^W$, an aryl group having 20 or less carbon atoms (preferably having 6 to 20 carbon atoms), the aryl group preferably further has the aliphatic hydrocarbon group as a substituent.

In the case of having an aliphatic hydrocarbon group, the aliphatic hydrocarbon group preferably has 4 to 12 carbon atoms and more preferably 8 to 12 carbon atoms.

The aliphatic hydrocarbon group is preferably an alkyl group and more preferably a linear alkyl group.

In General Formula (1), examples of the substituent that the alkyl group, the alkenyl group, the alkynyl group, the aryl group, and the heteroaryl group as $R^1$ to $R^{13}$ include a halogen atom, an alkyl group (including a cycloalkyl group, a bicycloalkyl group, and a tricycloalkyl group), an aryl group, a heterocyclic group (also referred to as "heterocyclic group"), a cyano group, a hydroxy group, a nitro group, a carboxy group, an alkoxy group, an aryloxy group, a silyl group, a silyloxy group, a heterocyclic oxy group, an acyloxy group, a carbamoyloxy group, an alkoxycarbonyloxy group, an aryloxycarbonyloxy group, an amino group (including an anilino group), an ammonio group, an acylamino group, an aminocarbonylamino group, an alkoxycarbonylamino group, an aryloxycarbonylamino group, a sulfamoylamino group, an alkyl- or arylsulfonylamino group, a mercapto group, an alkylthio group, an arylthio group, a heterocyclic thio group, a sulfamoyl group, a sulfo group, an alkyl- or arylsulfinyl group, an alkyl- or arylsulfonyl group, an acyl group, an aryloxycarbonyl group, an alkoxycarbonyl group, a carbamoyl group, an aryl- or heterocyclic azo group, an imide group, a phosphino group, a phosphinyl group, a phosphinyloxy group, a phosphinylamino group, a phosphono group, a silyl group, a hydrazino group, a ureido group, a boronic acid group ($-B(OH)_2$), a phosphate group ($-OPO(OH)_2$), a sulfate group ($-OSO_3H$), and other well-known substituents.

Among these, the substituent is preferably a halogen atom, an alkyl group, an alkoxy group, an alkylsilyl group, or an aryl group, more preferably a fluorine atom, a substituted or unsubstituted alkyl group having 1 to 10 carbon atoms, a substituted or unsubstituted alkoxy group having 1 to 10 carbon atoms, a substituted or unsubstituted alkylsilyl group having 1 to 30 carbon atoms, or a phenyl group, and particularly preferably a fluorine atom, a substituted or unsubstituted alkyl group having 1 to 10 carbon atoms, a substituted or unsubstituted alkoxy group having 1 to 10 carbon atoms, or a substituted or unsubstituted alkylsilyl group having 1 to 30 carbon atoms.

From the viewpoint of further improving the symmetry of the molecule and consequently improving the intermolecular interaction, it is preferable that $R^1$ and $R^2$ are the same group, $R^3$ and $R^{10}$ are the same group, $R^4$ and $R^9$ are the same group, $R^5$ and $R^8$ are the same group, and $R^6$ and $R^7$ are the same group.

The compound represented by General Formula (1) is preferably a compound which is represented by General Formula (2) or (3) (General Formulae (2) and (3) are structural isomers) and has a molecular weight of 3,000 or less.

General Formula (2)

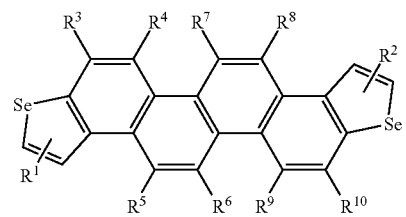

General Formula (3)

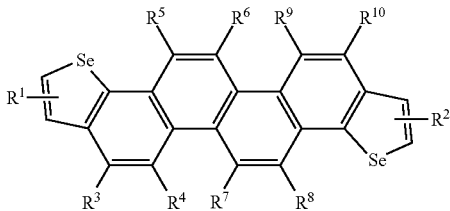

In General Formulae (2) and (3), $R^1$ to $R^{10}$ each independently represent a group represented by Formula (W).

$$-L^W-R^W \quad (W)$$

In Formula (W), $L^W$ is a divalent linking group of any of a single bond, —O—, —S—, —$NR^{11}$—, —CO—, —SO—, —$SO_2$—, or —$Si(R^{12})(R^{13})$— or a divalent linking group obtained by bonding two or more divalent linking groups described above, and $R^W$ represents a hydrogen atom, a halogen atom, or an alkyl group, an alkenyl group, an alkynyl group, an aryl group, or a heteroaryl group, all of which may have a substituent.

$R^{11}$ to $R^{13}$ each independently represent a hydrogen atom or an alkyl group, an alkenyl group, an alkynyl group, an aryl group, or a heteroaryl group, all of which may have a substituent.

Here, at least one of $R^1, \ldots,$ or $R^{10}$ has, as $R^W$, any group selected from the group consisting of an alkyl group having 20 or less carbon atoms, an aryl group having 20 or less carbon atoms, and a heteroaryl group having 20 or less carbon atoms, all of which may have a substituent, $R^1$ and $R^2$ are the same group, $R^3$ and $R^{10}$ are the same group, $R^4$ and $R^9$ are the same group, $R^5$ and $R^8$ are the same group, and $R^6$ and $R^7$ are the same group.

Meanwhile, the preferred aspects of $R^1$ to $R^{10}$ in General Formulae (2) and (3) are the same as the aspects described regarding $R^1$ to $R^{10}$ in General Formula (1).

The compound represented by General Formula (1) is preferably a compound which is represented by General Formula (4) or (5) (General Formulae (4) and (5) are structural isomers) and has a molecular weight of 3,000 or less.

General Formula (4)

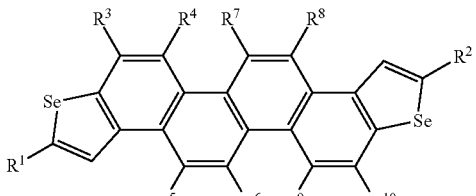

General Formula (5)

In General Formulae (4) and (5), $R^1$ to $R^{10}$ each independently represent a group represented by Formula (W).

$$-L^W-R^W \quad (W)$$

In Formula (W), $L^W$ is a divalent linking group of any of a single bond, —O—, —S—, —$NR^{11}$—, —CO—, —SO—, —$SO_2$—, or —$Si(R^{12})(R^{13})$— or a divalent linking group obtained by bonding two or more divalent linking groups described above, and $R^W$ represents a hydrogen atom, a halogen atom, or an alkyl group, an alkenyl group, an alkynyl group, an aryl group, or a heteroaryl group, all of which may have a substituent.

$R^{11}$ to $R^{13}$ each independently represent a hydrogen atom or an alkyl group, an alkenyl group, an alkynyl group, an aryl group, or a heteroaryl group, all of which may have a substituent.

Here, at least one of $R^1, \ldots,$ or $R^{10}$ has, as $R^W$, any group selected from the group consisting of an alkyl group having 20 or less carbon atoms, an aryl group having 20 or less carbon atoms, and a heteroaryl group having 20 or less carbon atoms, all of which may have a substituent, $R^1$ and $R^2$ are the same group, $R^3$ and $R^{10}$ are the same group, $R^4$ and $R^9$ are the same group, $R^5$ and $R^8$ are the same group, and $R^6$ and $R^7$ are the same group.

Meanwhile, the preferred aspects of $R^1$ to $R^{10}$ in General Formulae (4) and (5) are the same as the aspects described regarding $R^1$ to $R^{10}$ in General Formula (1).

The compound represented by General Formula (1) is preferably a compound which is represented by General Formula (6) or (7) (General Formulae (6) and (7) are structural isomers) and has a molecular weight of 3,000 or less.

General Formula (6)

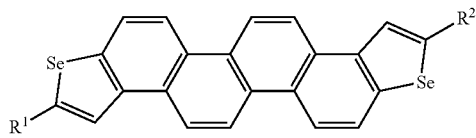

General Formula (7)

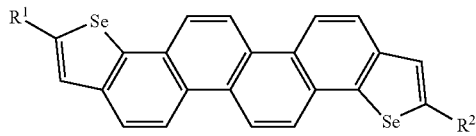

In General Formulae (6) and (7), $R^1$ and $R^2$ are the same group and each independently represent a group represented by Formula (W).

$$-L^W-R^W \quad (W)$$

In Formula (W), $L^W$ is a divalent linking group of any of a single bond, —O—, —S—, —$NR^{11}$—, —CO—, —SO—, —$SO_2$—, or —$Si(R^{12})(R^{13})$— or a divalent linking group obtained by bonding two or more divalent linking groups described above, and $R^W$ represents an alkyl group having 20 or less carbon atoms, an aryl group having 20 or less carbon atoms, or a heteroaryl group having 20 or less carbon atoms, all of which may have a substituent.

$R^{11}$ to $R^{13}$ each independently represent a hydrogen atom or an alkyl group, an alkenyl group, an alkynyl group, an aryl group, or a heteroaryl group, all of which may have a substituent.

Meanwhile, the preferred aspects of $R^1$ and $R^2$ in General Formulae (6) and (7) are the same as the aspects described regarding $R^1$ and $R^2$ in General Formula (1).

In General Formulae (6) and (7), $R^1$ and $R^2$ preferably include an aliphatic hydrocarbon group having 20 or less carbon atoms. The aliphatic hydrocarbon group is preferably an alkyl group and more preferably a linear alkyl group.

Specific examples of the compound represented by General Formula (1) will be illustrated.

In the tables, "TMS" represents a trimethylsilyl group, "TIPS" represents triisopropylsilyl group, "Bu" represents a butyl group, "Me" represents a methyl group, and "Ph" represents a phenyl group.

TABLE 1

Table 1 (1/24)
STRUCTURAL FORMULA

| Specific examples | R1 | R2 | R3 | R4 | R5 | R6 | R7 | R8 | R9 | R10 |
|---|---|---|---|---|---|---|---|---|---|---|
| 1 | n-C₁₀H₂₁ | n-C₁₀H₂₁ | H | H | H | H | H | H | H | H |
| 2 | n-C₆H₁₃ | n-C₆H₁₃ | H | H | H | H | H | H | H | H |
| 3 | –C₆H₄–n-C₁₀H₂₁ (para) | –C₆H₄–n-C₁₀H₂₁ (para) | H | H | H | H | H | H | H | H |
| 4 | –(2-thienyl)–n-C₁₀H₂₁ | –(2-thienyl)–n-C₁₀H₂₁ | H | H | H | H | H | H | H | H |

TABLE 2

Table 1 (2/24)

| Specific examples | R1 | R2 | R3 | R4 | R5 | R6 | R7 | R8 | R9 | R10 |
|---|---|---|---|---|---|---|---|---|---|---|
| 5 | –C₆H₄–n-C₁₀H₂₁ (meta) | –C₆H₄–n-C₁₀H₂₁ (meta) | H | H | H | H | H | H | H | H |
| 6 | –(thienyl)–n-C₁₀H₂₁ | –(thienyl)–n-C₁₀H₂₁ | H | H | H | H | H | H | H | H |
| 7 | –(CH₂)₄–O–(CH₂)₃CH₃ | –(CH₂)₄–O–(CH₂)₃CH₃ | H | H | H | H | H | H | H | H |
| 8 | t-Bu | t-Bu | H | H | H | H | H | H | H | H |
| 9 | TMS | TMS | H | H | H | H | H | H | H | H |
| 10 | –CH=CH–(CH₂)₅CH₃ | –CH=CH–(CH₂)₅CH₃ | H | H | H | H | H | H | H | H |

TABLE 3

Table 1 (3/24)

| Specific examples | R1 | R2 | R3 | R4 | R5 | R6 | R7 | R8 | R9 | R10 |
|---|---|---|---|---|---|---|---|---|---|---|
| 11 | —C≡C—n-$C_8H_{17}$ | —C≡C—n-$C_8H_{17}$ | H | H | H | H | H | H | H | H |
| 12 | 5-(n-$C_{10}H_{21}$)-pyridin-2-yl | 5-(n-$C_{10}H_{21}$)-pyridin-2-yl | H | H | H | H | H | H | H | H |
| 13 | 5-(n-$C_{10}H_{21}$)-selenophen-2-yl | 5-(n-$C_{10}H_{21}$)-selenophen-2-yl | H | H | H | H | H | H | H | H |
| 14 | 5-(n-$C_{10}H_{21}$)-furan-2-yl | 5-(n-$C_{10}H_{21}$)-furan-2-yl | H | H | H | H | H | H | H | H |
| 15 | —O—n-$C_5H_{11}$ | —O—n-$C_5H_{11}$ | H | H | H | H | H | H | H | H |
| 16 | —C≡C—TMS | —C≡C—TMS | H | H | H | H | H | H | H | H |

TABLE 4

Table 1 (4/24)

| Specific examples | R1 | R2 | R3 | R4 | R5 | R6 | R7 | R8 | R9 | R10 |
|---|---|---|---|---|---|---|---|---|---|---|
| 17 | 2,2-dimethylhexyl | 2,2-dimethylhexyl | H | H | H | H | H | H | H | H |
| 18 | 2-(n-$C_{10}H_{21}$)-thiazol-5-yl | 2-(n-$C_{10}H_{21}$)-thiazol-5-yl | H | H | H | H | H | H | H | H |
| 19 | n-$C_{10}H_{21}$ | Ph | H | H | H | H | H | H | H | H |
| 20 | —(CH$_2$)$_4$—O—n-C$_4$H$_9$ | Ph | H | H | H | H | H | H | H | H |
| 21 | Me | Me | —C≡C—TIPS | H | H | H | H | H | H | —C≡C—TIPS |
| 22 | Me | Me | H | —C≡C—TIPS | H | H | H | H | —C≡C—TIPS | H |

TABLE 5

Table 1 (5/24)

| Specific examples | R1 | R2 | R3 | R4 | R5 | R6 | R7 | R8 | R9 | R10 |
|---|---|---|---|---|---|---|---|---|---|---|
| 23 | Me | Me | H | H | —≡—TIPS | H | H | —≡—TIPS | H | H |
| 24 | Me | Me | H | H | H | —≡—TIPS | —≡—TIPS | H | H | H |
| 25 | Me | Me | H | H | —≡—n-C$_8$H$_{17}$ | H | H | —≡—n-C$_8$H$_{17}$ | H | H |
| 26 | H | H | H | H | —≡—TIPS | H | H | —≡—TIPS | H | H |
| 27 | OMe | OMe | H | H | —≡—TIPS | H | H | —≡—TIPS | H | H |
| 28 | F | F | H | H | —≡—TIPS | H | H | —≡—TIPS | H | H |

TABLE 6

Table 1 (6/24)

| Specific examples | R1 | R2 | R3 | R4 | R5 | R6 | R7 | R8 | R9 | R10 |
|---|---|---|---|---|---|---|---|---|---|---|
| 29 | Ph | Ph | H | H | —≡—TIPS | H | H | —≡—TIPS | H | H |

TABLE 7

Table 1 (7/24)
STRUCTURAL FORMULA

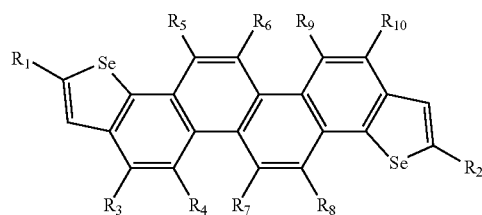

| Specific examples | R1 | R2 | R3 | R4 | R5 | R6 | R7 | R8 | R9 | R10 |
|---|---|---|---|---|---|---|---|---|---|---|
| 30 | n-C$_{10}$H$_{21}$ | n-C$_{10}$H$_{21}$ | H | H | H | H | H | H | H | H |
| 31 | n-C$_6$H$_{13}$ | n-C$_6$H$_{13}$ | H | H | H | H | H | H | H | H |

TABLE 7-continued

Table 1 (7/24)
STRUCTURAL FORMULA

[Structural formula showing a polycyclic aromatic compound with two selenophene (Se) rings and substituents $R_1$–$R_{10}$]

| Specific examples | R1 | R2 | R3 | R4 | R5 | R6 | R7 | R8 | R9 | R10 |
|---|---|---|---|---|---|---|---|---|---|---|
| 32 | –C$_6$H$_4$–n-C$_{10}$H$_{21}$ (para) | –C$_6$H$_4$–n-C$_{10}$H$_{21}$ (para) | H | H | H | H | H | H | H | H |
| 33 | 5-(n-C$_{10}$H$_{21}$)-thiophen-2-yl | 5-(n-C$_{10}$H$_{21}$)-thiophen-2-yl | H | H | H | H | H | H | H | H |

TABLE 8

Table 1 (8/24)

| Specific examples | R1 | R2 | R3 | R4 | R5 | R6 | R7 | R8 | R9 | R10 |
|---|---|---|---|---|---|---|---|---|---|---|
| 34 | –C$_6$H$_4$–n-C$_{10}$H$_{21}$ (meta) | –C$_6$H$_4$–n-C$_{10}$H$_{21}$ (meta) | H | H | H | H | H | H | H | H |
| 35 | 4-(n-C$_{10}$H$_{21}$)-thiophen-2-yl | 4-(n-C$_{10}$H$_{21}$)-thiophen-2-yl | H | H | H | H | H | H | H | H |
| 36 | –(CH$_2$)$_4$–O–(CH$_2$)$_3$CH$_3$ | –(CH$_2$)$_4$–O–(CH$_2$)$_3$CH$_3$ | H | H | H | H | H | H | H | H |
| 37 | t-Bu | t-Bu | H | H | H | H | H | H | H | H |

TABLE 9

Table 1 (9/24)

| Specific examples | R1 | R2 | R3 | R4 | R5 | R6 | R7 | R8 | R9 | R10 |
|---|---|---|---|---|---|---|---|---|---|---|
| 38 | TMS | TMS | H | H | H | H | H | H | H | H |
| 39 | –CH=CH–(CH$_2$)$_5$CH$_3$ | –CH=CH–(CH$_2$)$_5$CH$_3$ | H | H | H | H | H | H | H | H |

TABLE 9-continued

Table 1 (9/24)

| Specific examples | R1 | R2 | R3 | R4 | R5 | R6 | R7 | R8 | R9 | R10 |
|---|---|---|---|---|---|---|---|---|---|---|
| 40 | —≡—n-C$_8$H$_{17}$ | —≡—n-C$_8$H$_{17}$ | H | H | H | H | H | H | H | H |
| 41 | pyridine-n-C$_{10}$H$_{21}$ | pyridine-n-C$_{10}$H$_{21}$ | H | H | H | H | H | H | H | H |
| 42 | selenophene-n-C$_{10}$H$_{21}$ | selenophene-n-C$_{10}$H$_{21}$ | H | H | H | H | H | H | H | H |
| 43 | furan-n-C$_{10}$H$_{21}$ | furan-n-C$_{10}$H$_{21}$ | H | H | H | H | H | H | H | H |

TABLE 10

Table 1 (10/24)

| Specific examples | R1 | R2 | R3 | R4 | R5 | R6 | R7 | R8 | R9 | R10 |
|---|---|---|---|---|---|---|---|---|---|---|
| 44 | —O-n-C$_5$H$_{11}$ | —O-n-C$_5$H$_{11}$ | H | H | H | H | H | H | H | H |
| 45 | —≡—TMS | —≡—TMS | H | H | H | H | H | H | H | H |
| 46 | —C(CH$_3$)$_2$-n-C$_5$H$_{11}$ | —C(CH$_3$)$_2$-n-C$_5$H$_{11}$ | H | H | H | H | H | H | H | H |
| 47 | thiazole-n-C$_{10}$H$_{21}$ | thiazole-n-C$_{10}$H$_{21}$ | H | H | H | H | H | H | H | H |
| 48 | n-C$_{10}$H$_{21}$ | Ph | H | H | H | H | H | H | H | H |
| 49 | —(CH$_2$)$_4$O-n-C$_4$H$_9$ | Ph | H | H | H | H | H | H | H | H |

TABLE 11

Table 1 (11/24)

| Specific examples | R1 | R2 | R3 | R4 | R5 | R6 |
|---|---|---|---|---|---|---|
| 50 | Me | Me | —≡—TIPS | H | H | H |
| 51 | Me | Me | H | —≡—TIPS | H | H |
| 52 | Me | Me | H | H | —≡—TIPS | H |
| 53 | Me | Me | H | H | H | —≡—TIPS |
| 54 | Me | Me | H | H | —≡—n-C$_8$H$_{17}$ | H |
| 55 | H | H | H | H | —≡—TIPS | H |

| Specific examples | R7 | R8 | R9 | R10 |
|---|---|---|---|---|
| 50 | H | H | H | —≡—TIPS |
| 51 | H | H | —≡—TIPS | H |
| 52 | H | —≡—TIPS | H | H |
| 53 | —≡—TIPS | H | H | H |
| 54 | H | —≡—n-C$_8$H$_{17}$ | H | H |
| 55 | H | —≡—TIPS | H | H |

TABLE 12

Table 1 (12/24)

| Specific examples | R1 | R2 | R3 | R4 | R5 | R6 | R7 | R8 | R9 | R10 |
|---|---|---|---|---|---|---|---|---|---|---|
| 56 | OMe | OMe | H | H | —≡—TIPS | H | H | —≡—TIPS | H | H |
| 57 | F | F | H | H | —≡—TIPS | H | H | —≡—TIPS | H | H |
| 58 | Ph | Ph | H | H | —≡—TIPS | H | H | —≡—TIPS | H | H |

TABLE 13
Table 1 (13/24)
STRUCTURAL FORMULA
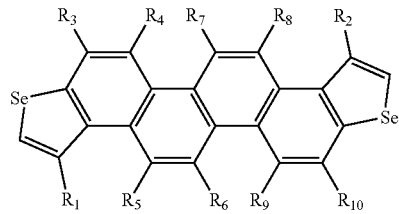
| Specific examples | R1 | R2 | R3 | R4 | R5 | R6 | R7 | R8 | R9 | R10 |
|---|---|---|---|---|---|---|---|---|---|---|
| 59 | n-$C_{10}H_{21}$ | n-$C_{10}H_{21}$ | H | H | H | H | H | H | H | H |
| 60 | n-$C_6H_{13}$ | n-$C_6H_{13}$ | H | H | H | H | H | H | H | H |
| 61 | 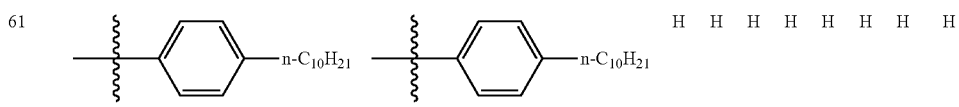 | | H | H | H | H | H | H | H | H |
| 62 | | | H | H | H | H | H | H | H | H |
TABLE 14
Table 1 (14/24)
| Specific examples | R1 | R2 | R3 | R4 | R5 | R6 | R7 | R8 | R9 | R10 |
|---|---|---|---|---|---|---|---|---|---|---|
| 63 | | | H | H | H | H | H | H | H | H |
| 64 | | | H | H | H | H | H | H | H | H |
| 65 | | | H | H | H | H | H | H | H | H |

TABLE 15
Table 1 (15/24)
STRUCTURAL FORMULA
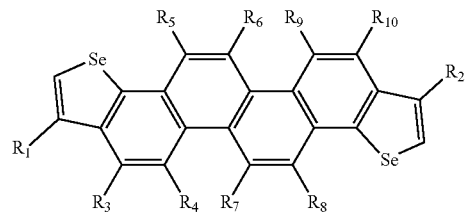
| Specific examples | R1 | R2 | R3 | R4 | R5 | R6 | R7 | R8 | R9 | R10 |
|---|---|---|---|---|---|---|---|---|---|---|
| 66 | n-$C_{10}H_{21}$ | n-$C_{10}H_{21}$ | H | H | H | H | H | H | H | H |
| 67 | n-$C_6H_{13}$ | n-$C_6H_{13}$ | H | H | H | H | H | H | H | H |
| 68 | 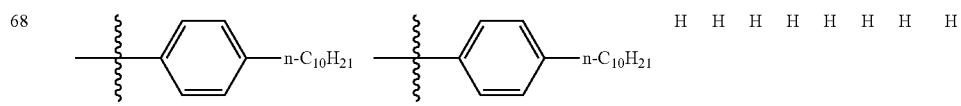 | | H | H | H | H | H | H | H | H |
| 69 | | | H | H | H | H | H | H | H | H |
35
TABLE 16
Table 1 (16/24)
| Specific examples | R1 | R2 | R3 | R4 | R5 | R6 | R7 | R8 | R9 | R10 |
|---|---|---|---|---|---|---|---|---|---|---|
| 70 | 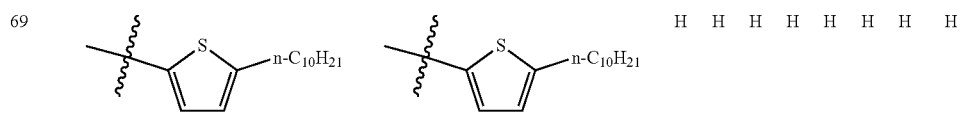 | | H | H | H | H | H | H | H | H |
| 71 | | | H | H | H | H | H | H | H | H |
| 72 | | | H | H | H | H | H | H | H | H |

TABLE 17
Table 1 (17/24)
STRUCTURAL FORMULA
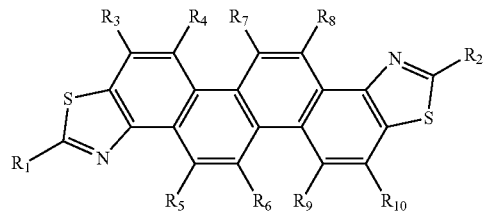
| Specific examples | R1 | R2 | R3 | R4 | R5 | R6 | R7 | R8 | R9 | R10 |
|---|---|---|---|---|---|---|---|---|---|---|
| 73 | n-$C_{10}H_{21}$ | n-$C_{10}H_{21}$ | H | H | H | H | H | H | H | H |
| 74 | n-$C_6H_{13}$ | n-$C_6H_{13}$ | H | H | H | H | H | H | H | H |
| 75 | —C₆H₄—n-$C_{10}H_{21}$ | —C₆H₄—n-$C_{10}H_{21}$ | H | H | H | H | H | H | H | H |
| 76 | —(thienyl)—n-$C_{10}H_{21}$ | —(thienyl)—n-$C_{10}H_{21}$ | H | H | H | H | H | H | H | H |
TABLE 18
Table 1 (18/24)
| Specific examples | R1 | R2 | R3 | R4 | R5 | R6 | R7 | R8 | R9 | R10 |
|---|---|---|---|---|---|---|---|---|---|---|
| 77 | —C₆H₄(m)—n-$C_{10}H_{21}$ | —C₆H₄(m)—n-$C_{10}H_{21}$ | H | H | H | H | H | H | H | H |
| 78 | —(thienyl)—n-$C_{10}H_{21}$ | —(thienyl)—n-$C_{10}H_{21}$ | H | H | H | H | H | H | H | H |
| 79 | —(CH₂)₄—O—(CH₂)₃CH₃ | —(CH₂)₄—O—(CH₂)₃CH₃ | H | H | H | H | H | H | H | H |

TABLE 19
Table 1 (19/24)
STRUCTURAL FORMULA
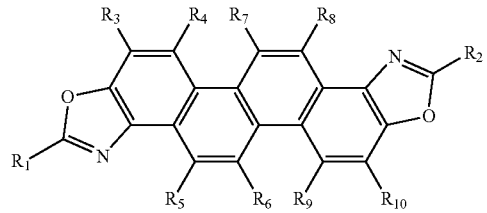
| Specific examples | R1 | R2 | R3 | R4 | R5 | R6 | R7 | R8 | R9 | R10 |
|---|---|---|---|---|---|---|---|---|---|---|
| 80 | n-$C_{10}H_{21}$ | n-$C_{10}H_{21}$ | H | H | H | H | H | H | H | H |
| 81 | n-$C_6H_{13}$ | n-$C_6H_{13}$ | H | H | H | H | H | H | H | H |
| 82 | 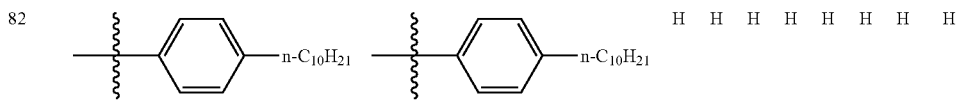 | | H | H | H | H | H | H | H | H |
| 83 | 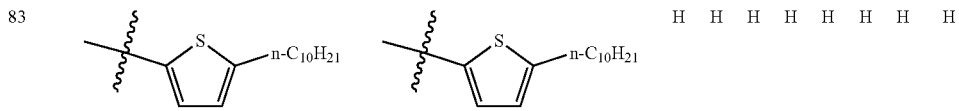 | | H | H | H | H | H | H | H | H |
TABLE 20
Table 1 (20/24)
| Specific examples | R1 | R2 | R3 | R4 | R5 | R6 | R7 | R8 | R9 | R10 |
|---|---|---|---|---|---|---|---|---|---|---|
| 84 | 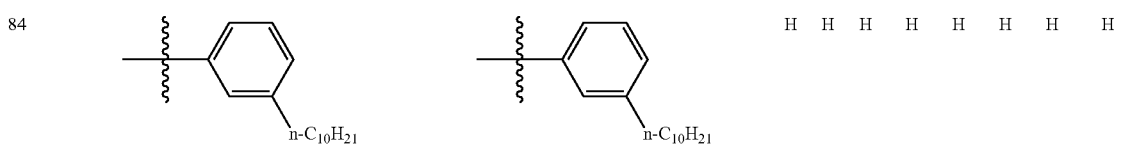 | | H | H | H | H | H | H | H | H |
| 85 | 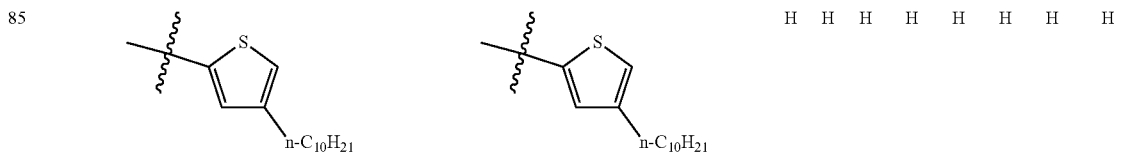 | | H | H | H | H | H | H | H | H |
| 86 | 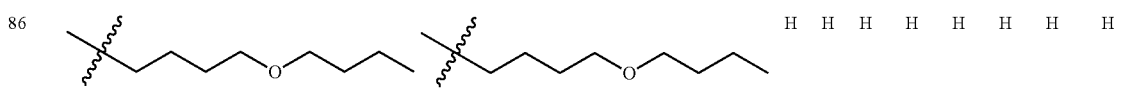 | | H | H | H | H | H | H | H | H |

TABLE 21

Table 1 (21/24)
STRUCTURAL FORMULA

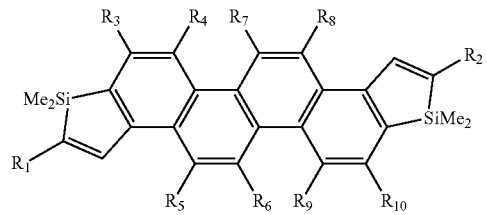

| Specific examples | R1 | R2 | R3 | R4 | R5 | R6 | R7 | R8 | R9 | R10 |
|---|---|---|---|---|---|---|---|---|---|---|
| 87 | n-$C_{10}H_{21}$ | n-$C_{10}H_{21}$ | H | H | H | H | H | H | H | H |
| 88 | n-$C_6H_{13}$ | n-$C_6H_{13}$ | H | H | H | H | H | H | H | H |
| 89 | 4-(n-$C_{10}H_{21}$)phenyl | 4-(n-$C_{10}H_{21}$)phenyl | H | H | H | H | H | H | H | H |
| 90 | 5-(n-$C_{10}H_{21}$)thiophen-2-yl | 5-(n-$C_{10}H_{21}$)thiophen-2-yl | H | H | H | H | H | H | H | H |

TABLE 22

Table 1 (22/24)

| Specific examples | R1 | R2 | R3 | R4 | R5 | R6 | R7 | R8 | R9 | R10 |
|---|---|---|---|---|---|---|---|---|---|---|
| 91 | 3-(n-$C_{10}H_{21}$)phenyl | 3-(n-$C_{10}H_{21}$)phenyl | H | H | H | H | H | H | H | H |
| 92 | 4-(n-$C_{10}H_{21}$)thiophen-2-yl | 4-(n-$C_{10}H_{21}$)thiophen-2-yl | H | H | H | H | H | H | H | H |
| 93 | -(CH$_2$)$_4$-O-(CH$_2$)$_3$CH$_3$ | -(CH$_2$)$_4$-O-(CH$_2$)$_3$CH$_3$ | H | H | H | H | H | H | H | H |

TABLE 23

Table 1 (23/24)
STRUCTURAL FORMULA

[Structural formula with R1–R10 substituents on a fused ring system bearing two imidazole (HN) groups]

| Specific examples | R1 | R2 | R3 | R4 | R5 | R6 | R7 | R8 | R9 | R10 |
|---|---|---|---|---|---|---|---|---|---|---|
| 94 | n-$C_{10}H_{21}$ | n-$C_{10}H_{21}$ | H | H | H | H | H | H | H | H |
| 95 | n-$C_6H_{13}$ | n-$C_6H_{13}$ | H | H | H | H | H | H | H | H |

TABLE 24

Table 1 (24/24)
STRUCTURAL FORMULA

[Structural formula with R1–R10 substituents on a fused ring system bearing two N-methyl imidazole (MeN) groups]

| Specific examples | R1 | R2 | R3 | R4 | R5 | R6 | R7 | R8 | R9 | R10 |
|---|---|---|---|---|---|---|---|---|---|---|
| 96 | n-$C_{10}H_{21}$ | n-$C_{10}H_{21}$ | H | H | H | H | H | H | H | H |
| 97 | n-$C_6H_{13}$ | n-$C_6H_{13}$ | H | H | H | H | H | H | H | H |

The method for synthesizing the compound represented by General Formula (1) is not particularly limited, and the compound can be synthesized with reference to well-known methods.

Preferred examples of the synthesis method include a method including a step of heating and reacting a compound represented by General Formula (8) or (9) and a compound represented by General Formula (10) in the presence of a transition metal catalyst and an organic solvent.

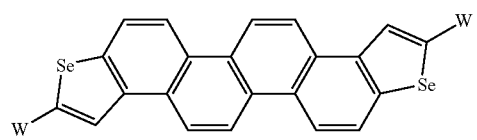

General Formula (8)

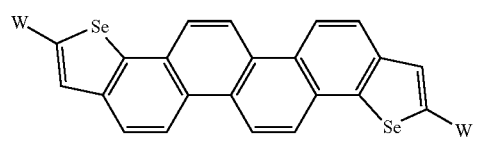

General Formula (9)

In General Formulae (8) and (9),
W's each independently represents a halogen atom or a perfluoroalkylsulfonyloxy group.

$R^{11}$-M($R^{12}$)$_i$    General Formula (10)

In General Formula (10), $R^{11}$ represents an alkyl group, an alkenyl group, an alkynyl group, an aryl group, or a heteroaryl group and may further have a substituent, M represents magnesium, silicon, boron, tin, or zinc, $R^{12}$'s each independently represent a halogen atom, an alkyl group, an alkenyl group, an alkynyl group, an alkoxy group, or a hydroxyl group, may be identical to or different from one another, and may form a ring in association with one another, and i represents an integer of 1 to 3, is the valence of M-1; however, in a case in which M is boron, i may be 3.

The transition metal catalyst is not particularly limited, and it is possible to preferably use transition metal catalysts that are used in coupling reactions such as Kumada-Tamao-Corriu coupling, Hiyama coupling, Suzuki-Miyaura coupling, Migita-Kosugi-Stille coupling, Sonogashira-Hagihara coupling, Mizoroki-Heck reactions, or Negishi coupling. Among them, palladium catalysts or nickel catalysts are preferred, and palladium catalysts are more preferred. In addition, the metal catalyst may have an arbitrary ligand depending on reactions.

The organic solvent is not particularly limited and can be appropriately selected depending on matrixes or the catalyst.

In addition, the amounts of the compounds represented by General Formulae (8) to (10), the transition metal catalyst, and the organic solvent used are not particularly limited and may be appropriately selected as necessary.

The heating temperature during reactions is not particularly limited, but is preferably 25° C. to 200° C. and more preferably 40° C. to 150° C.

The number of kinds of the compound represented by General Formula (1) included in the organic semiconductor film of the organic thin-film transistor of the present invention may be one or more, but is preferably one from the viewpoint of the orientation.

In addition, the number of kinds of the compound represented by General Formula (1) included in an organic semiconductor film, a material for an organic thin-film transistor, or a composition for an organic thin-film transistor described below may be one or more, but is preferably one from the viewpoint of the orientation.

The total content of the compound represented by General Formula (1) in the organic semiconductor film of the organic thin-film transistor of the present invention is preferably 30% to 100% by mass, more preferably 50% to 100% by mass, and still more preferably 70% to 100% by mass. In addition, in the case of containing no binder polymer described below, the total content is preferably 90% to 100% by mass and more preferably 95% to 100% by mass.

<Structure of Organic Thin-Film Transistor and Method for Manufacturing Organic Thin-Film Transistor>

Next, the structure of the organic thin-film transistor of the present invention in which the compound represented by General Formula (1) is used in the organic semiconductor film of the organic thin-film transistor and a manufacturing method therefor will be described.

The organic thin-film transistor of the present invention has the organic semiconductor film (organic semiconductor layer) including the compound represented by General Formula (1) and may further have a source electrode, a drain electrode, and a gate electrode.

The structure of the organic thin-film transistor according to the present invention is not particularly limited and may be any structure of, for example, a bottom contact-type (bottom contact-bottom gate-type and bottom contact-top gate-type) structure, a top contact-type (top contact-bottom gate-type and top contact-top gate-type) structure, or the like.

Hereinafter, an example of the organic thin-film transistor of the present invention will be described with reference to the drawings.

FIG. 1 is a schematic cross-sectional view of a bottom contact-type organic thin-film transistor 100 according to an embodiment of the present invention.

In the example of FIG. 1, the organic thin-film transistor 100 has a substrate (base material) 10, a gate electrode 20, a gate insulating film 30, a source electrode 40, a drain electrode 42, an organic semiconductor film (organic semiconductor layer) 50, and a sealing layer 60. Here, the organic semiconductor film 50 is produced using the compound represented by General Formula (1).

Hereinafter, the substrate (base material), the gate electrode, the gate insulating film, the source electrode, the drain electrode, the organic semiconductor film (organic semiconductor layer), and the sealing layer and production methods therefor will be described in detail.

(Substrate)

The substrate plays a role of supporting the gate electrode, the source electrode, the drain electrode, all of which will be described below, or the like.

The kind of the substrate is not particularly limited, and examples thereof include a plastic substrate, a glass substrate, a ceramic substrate, and the like. Among these, from the viewpoint of applicability to individual devices and costs, a glass substrate or a plastic substrate is preferred.

(Gate Electrode)

The material of the gate electrode include metal such as gold (Au), silver, aluminum, copper, chromium, nickel, cobalt, titanium, platinum, magnesium, calcium, barium, and sodium; conductive oxides such as $InO_2$, $SnO_2$, and indium tin oxide (ITO); conductive macromolecules such as polyaniline, polypyrrole, polythiophene, polyacetylene, and polydiacetylene; semiconductors such as silicon, germanium, and gallium arsenide; carbon materials such as fullerene, carbon nanotubes, and graphite; and the like. Among these, metal is preferred, and silver or aluminum is more preferred.

The thickness of the gate electrode is not particularly limited, but is preferably 20 to 200 nm.

Meanwhile, the gate electrode may also function as the substrate, and, in such a case, the above-described substrate may not be provided.

The method for forming the gate electrode is not particularly limited, and examples thereof include a method in which an electrode material is deposited in a vacuum or sputtered on a substrate, a method in which a composition for forming the electrode is applied or printed, and the like. In addition, examples of the patterning method in the case of patterning the electrode include printing methods such as a photolithography method, ink jet printing, screen printing, offset printing, and anastatic printing (flexo printing); a mask deposition method; and the like.

(Gate Insulating Film)

Examples of the material for the gate insulating film include polymers such as polymethyl methacrylate, polystyrene, polyvinyl phenol, polyimide, polycarbonate, polyester, polyvinyl alcohol, polyvinyl acetate, polyurethane, polysulfone, polybenzoxazole, polysilsesquioxane, an epoxy resin, and a phenolic resin; oxides such as silicon dioxide, aluminum oxide, and titanium oxide; nitrides such as silicon nitride; and the like. Among these materials, polymers are preferred from the viewpoint of compatibility with the organic semiconductor film.

The film thickness of the gate insulating film is not particularly limited, but is preferably 100 to 1,000 nm.

The method for forming the gate insulating film is not particularly limited, and examples thereof include a method in which a composition for forming the gate insulating film is applied onto the substrate on which the gate electrode is formed, a method in which a gate insulating film material is deposited or sputtered, and the like.

(Source Electrode and Drain Electrode)

Specific examples of the material of the source electrode and the drain electrode are the same as those for the gate electrode. Among them, metal is preferred, and silver is more preferred.

The method for forming the source electrode and the drain electrode is not particularly limited, and examples thereof include a method in which an electrode material is deposited in a vacuum or sputtered on a substrate on which the gate electrode and the gate insulating film are formed, a method in which a composition for forming the electrode is applied or printed, and the like. Specific examples of the patterning method are the same as those for the gate electrode.

(Organic Semiconductor Film)

The method for producing the organic semiconductor film is not particularly limited as long as organic semiconductor films including the compound represented by General Formula (1) can be produced, and, for example, the organic semiconductor film can be produced by applying a composition for the organic thin-film transistor including the compound represented by General Formula (1) (described below) on a substrate and drying the composition.

Meanwhile, the application of the composition for the organic thin-film transistor onto a substrate refers not only to an aspect in which the composition for the organic thin-film transistor is directly imparted to a substrate but also to an aspect in which the composition for the organic thin-film transistor is imparted above a substrate through a separate layer provided on the substrate.

As the method for applying the composition for the organic thin-film transistor, well-known methods can be used, and examples thereof include a bar coating method, a spin coating method, a knife coating method, a doctor blade method, an ink jet printing method, a flexo printing method, a gravure printing method, and a screen printing method. Furthermore, as the method for applying the composition for the organic thin-film transistor, the method for forming the organic semiconductor film described in JP2013-207085A (a so-called gap cast method), the method for manufacturing the organic semiconductor film described in WO2014/175351A (a so-called edge cast method or continuous edge cast method), or the like is preferably used.

For drying (drying treatment), the optimal conditions are appropriately selected depending on the kinds of individual components included in the composition for the organic thin-film transistor, and the composition may be naturally dried, but is preferably heated from the viewpoint of improving productivity. For example, the heating temperature is preferably 30° C. to 200° C. and more preferably 40° C. to 150° C., and the heating time is preferably 10 to 300 minutes and more preferably 30 to 180 minutes.

The film thickness of the organic semiconductor film being produced is not particularly limited, but is preferably 10 to 500 nm and more preferably 20 to 200 nm since the effects of the present invention are more favorable.

As described above, the organic semiconductor film containing the compound represented by General Formula (1) is preferably used in the organic thin-film transistor, but the use thereof is not limited thereto, and the organic semiconductor film containing the compound represented by General Formula (1) can also be applied to other uses described below.

(Sealing Layer)

From the viewpoint of durability, the organic thin-film transistor of the present invention preferably includes a sealing layer in the outermost layer. For the sealing layer, a well-known sealing agent (composition for forming the sealing layer) can be used.

The thickness of the sealing layer is not particularly limited, but is preferably 0.2 to 10 µm.

(Other Organic Thin-Film Transistors)

Figure 2:
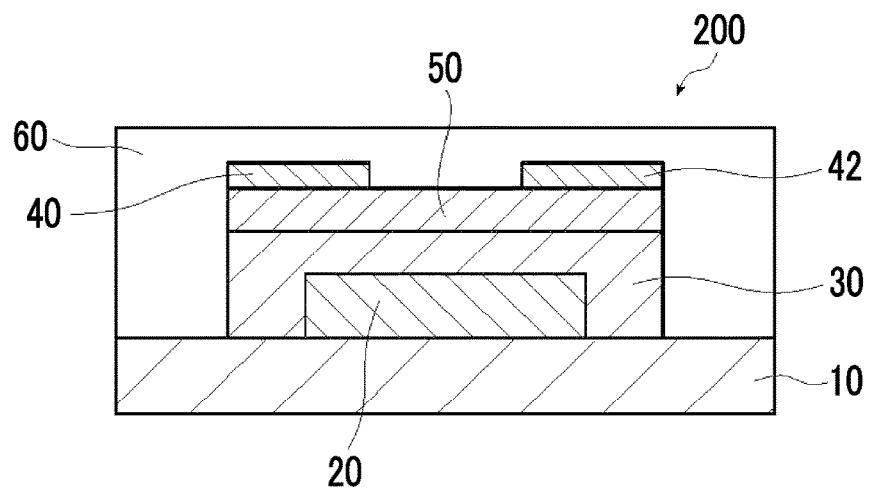
FIG. 2 is a schematic cross-sectional view of a top contact-type organic thin-film transistor according to an embodiment of the present invention.

FIG. 2 is a schematic cross-sectional view of a top contact-type organic thin-film transistor 200 according to an embodiment of the present invention.

In the example of FIG. 2, the organic thin-film transistor 200 has the substrate 10, the gate electrode 20, the gate insulating film 30, the source electrode 40, the drain electrode 42, the organic semiconductor film (organic semiconductor layer) 50, and the sealing layer 60.

Here, the organic semiconductor film 50 is formed using a composition for an organic thin-film transistor of the present invention described below.

The substrate, the gate electrode, the gate insulating film, the source electrode, the drain electrode, the organic semiconductor film, and the sealing layer have already been described above and thus will not be described again.

(Applications of Organic Thin-Film Transistor)

The organic thin-film transistor can be singly used as switching elements. In addition, the organic thin-film transistor can be used for, for example, electronic paper, display portions that display images of display devices, light-receiving portions that receive the light of images of X-ray flat panel detectors, and the like by arraying a plurality of elements on a matrix. In addition, the organic thin-film transistor can be applied to small-sized circuits such as inverters, ring oscillators, and d-flip-flops or logic circuits such as radio frequency identifiers (RFID, RF tags) or memories by combining a plurality of elements. The respective devices may have a well-known structure, and thus the structures thereof will not be described.

[Composition for Organic Thin-Film Transistor]

A composition for an organic thin-film transistor of the present invention is used to produce the organic semiconductor film of the organic thin-film transistor.

Meanwhile, the composition for an organic thin-film transistor which will be described below may be used for other uses described below, and, in such cases, the "composition for an organic thin-film transistor" will be simply referred to as "organic semiconductor composition".

The composition for an organic thin-film transistor contains the compound represented by General Formula (1) and, generally, further contains an organic solvent from the viewpoint of improving the coatability.

In the case of containing an organic solvent, the content thereof is preferably 0.01% to 80% by mass, more preferably 0.05% to 10% by mass, and still more preferably 0.1% to 5% by mass with respect to the total mass of the composition for an organic thin-film transistor from the viewpoint of improving the coatability.

(Organic Solvent)

The organic solvent is not particularly limited, and examples thereof include hydrocarbon-based solvents such as hexane, octane, decane, toluene, xylene, mesitylene, ethylbenzene, decalin, tetralin, 2-methyl benzothiazole, and 1-methyl naphthalene, ketone-based solvents such as acetone, methyl ethyl ketone, methyl isobutyl ketone, and cyclohexanone, halogenated hydrocarbon-based solvents such as dichloromethane, chloroform, tetrachloromethane, dichloroethane, trichloroethane, tetrachloroethane, chlorobenzene, dichlorobenzene, 1,2-dichlorobenzene, 1-fluoronaphthalene, 2,5-dichlorothiophene, 2,5-dibromothiophene, 1-chloronaphthalene, and chlorotoluene, ester-based solvents such as ethyl acetate, butyl acetate, amyl acetate, and ethyl lactate, alcohol-based solvents such as methanol, propanol, butanol, pentanol, hexanol, cyclohexanol, methyl cellosolve, ethyl cellosolve, and ethylene glycol, ether-based solvents such as butoxybenzene, dibutyl ether, tetrahydrofuran, dioxane, and anisole, amide-based solvents such as N,N-dimethyl formamide and N,N-dimethylacetamide, imide-based solvents such as 1-methyl-2-pyrrolidone and 1-methyl-2-imidazolidinone, sulfoxide-based solvents such as dimethyl sulfoxide, nitrile-based solvents such as acetonitrile, and the like.

The organic solvent may be used singly or two or more solvents may be jointly used.

(Binder Polymer)

The composition for an organic thin-film transistor may further contain a binder polymer.

The kind of the binder polymer is not particularly limited, and well-known binder polymers can be used. Examples of the binder polymer include insulating polymers such as polystyrene, polycarbonate, polyarylate, polyester, polyamide, polyimide, polyurethane, polysiloxane, polysulfone, polymethyl methacrylate, polymethyl acrylate, cellulose, polyethylene, and polypropylene and copolymers thereof; rubber or thermoplastic elastomers such as ethylene-propylene rubber, acrylonitrile-butadiene rubber, hydrogenated nitrile rubber, fluororubber, a perfluoroelastomer, a tetrafluoroethylene propylene copolymer, an ethylene-propylene-diene copolymer, styrene-butadiene rubber, polychloroprene, polyneoprene, butyl rubber, a methyl phenyl silicone resin, a methyl phenyl vinyl silicone resin, a methyl vinyl silicone resin, a fluorosilicone resin, acrylic rubber, ethylene acrylic rubber, chlorosulfonated polyethylene, chloropolyethylene, an epichlorohydrin copolymer, a polyisoprene-natural rubber copolymer, polyisoprene rubber, a styrene-isoprene block copolymer, a polyether urethane copolymer, a polyether ester thermoplastic elastomer, and polybutadiene rubber; photoconductive polymers such as polyvinyl carbazole and polysilane; conductive polymers such as polythiophene, polypyrrole, polyaniline, and polyparaphenylene vinylene; and semiconductor polymers described in, for example, Chemistry of Materials, 2014, 26, 647.

The polymer binder may be used singly or a plurality of polymer binders may be jointly used.

Among these, the binder polymer is preferably a macromolecular compound having a benzene ring (a macromolecule having a monomer unit having a benzene ring). The content of the monomer unit having a benzene ring is not particularly limited, but is preferably 50% by mole or more, more preferably 70% by mole or more, and still more preferably 90% by mole or more. The upper limit is not particularly limited, but is, for example, 100% by mole.

Specific examples of the binder polymer include polystyrene, poly(α-methylstyrene), polyvinyl cinnamate, poly(4-vinylphenyl), poly(4-methylstyrene), poly[bis(4-phenyl)(2,4,6-trimethylphenyl)amine], and poly[2,6-(4,4-bis(2-ethylhexyl)-4Hcyclopenta[2,1-b;3,4-b']dithophene)-alt-4,7-(2,1,3-benzothiazole)], and the like, polystyrene or poly(α-methylstyrene) is more preferred, and poly(α-methylstyrene) is still more preferred.

The weight-average molecular weight of the binder polymer is not particularly limited, but is preferably 1,000 to 2,000,000, more preferably 3,000 to 1,000,000, and still more preferably 5,000 to 600,000.

In the case of containing the binder polymer, the content is preferably 1 to 10,000 parts by mass, more preferably 10 to 1,000 parts by mass, still more preferably 25 to 400 parts by mass, and most preferably 50 to 200 parts by mass with respect to 100 parts by mass of the compound represented by General Formula (1) included in the composition for an organic thin-film transistor. In the above-described range, the carrier mobility of organic semiconductor films and organic semiconductor elements to be obtained and the uniformity of films are superior.

(Other Components)

The composition for an organic thin-film transistor may contain components other than the components described above. As the other components, well-known additives and the like can be used.

(Preparation Method)

The method for preparing the composition for an organic thin-film transistor is not particularly limited and well-known methods can be used. For example, a predetermined amount of the compound represented by General Formula (1) and the like are added to the organic solvent, and a stirring treatment is appropriately carried out, whereby the composition for an organic thin-film transistor of the present invention can be obtained.

[Material for Organic Thin-Film Transistor]

A material for an organic thin-film transistor of the present invention contains the compound represented by General Formula (1). The material for an organic thin-film transistor refers to a material which is used for organic thin-film transistors and exhibits the characteristics of semiconductors.

The compound represented by General Formula (1) is a material exhibiting the properties of semiconductors and is a p-type (hole transport-type) organic semiconductor material that conducts electricity using electrons as carriers.

Meanwhile, the material for an organic thin-film transistor may be used for other uses described below, and, in such cases, the "material for an organic thin-film transistor" will be simply referred to as "organic semiconductor material".

[Other Uses of Compound Represented by General Formula (1)]

The compound represented by General Formula (1) has excellent properties as described above and thus can also be preferably used for uses other than organic thin-film transistors.

Examples of the other uses include non-luminous organic semiconductor devices. The non-luminous organic semiconductor devices refer to devices that are not intended to emit light.

Examples of the non-luminous organic semiconductor devices include, in addition to the above-described organic thin-film transistor, organic photoelectric conversion elements (solid image pickup elements for light sensors, solar batteries for energy conversion, and the like), gas sensors, organic rectifier cells, information recording elements, and the like.

In the non-luminous organic semiconductor devices, the organic semiconductor film is preferably caused to function as an electronics element. The scope of the organic semiconductor film includes organic semiconductor films including the compound represented by General Formula (1).

EXAMPLES

Hereinafter, the characteristics of the present invention will be more specifically described using examples and comparative examples. Materials, amounts used, proportions, processing contents, processing orders, and the like described in the following examples can be appropriately modified within the scope of the gist of the present invention. Therefore, the scope of the present invention is not supposed to be restrictively interpreted by specific examples described below.

Examples 1 to 5 and Comparative Examples 1 to 3

Synthesis Examples

Synthesis of Compound 1

A compound 1 (corresponding to Exemplary Compound 3 in Table 1) which is the compound represented by General Formula (1) was synthesized according to a specific synthesis order illustrated in the following scheme.

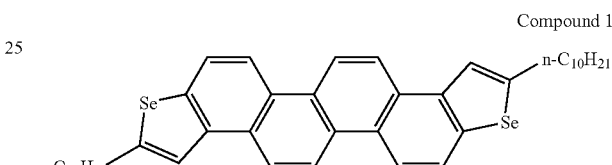

(corresponding to Exemplary Compound 3 in Table 1)

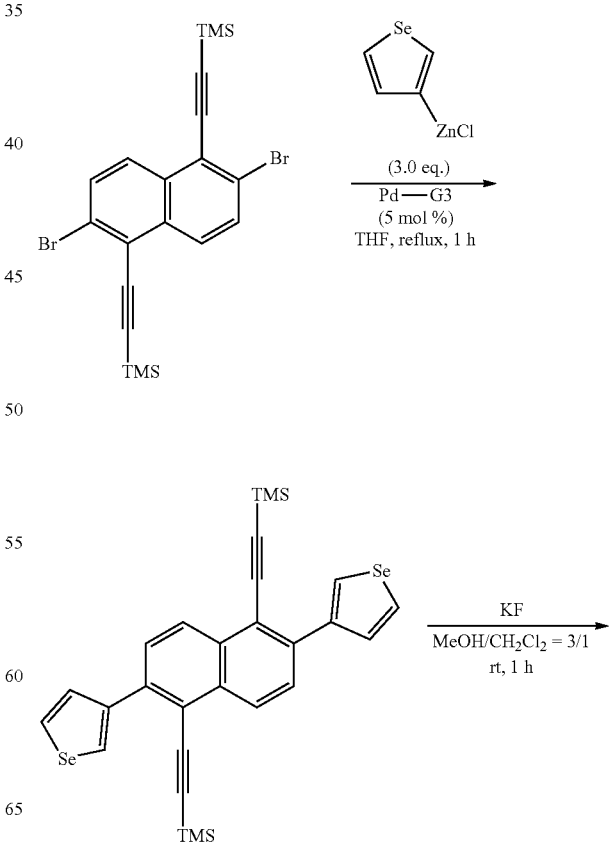

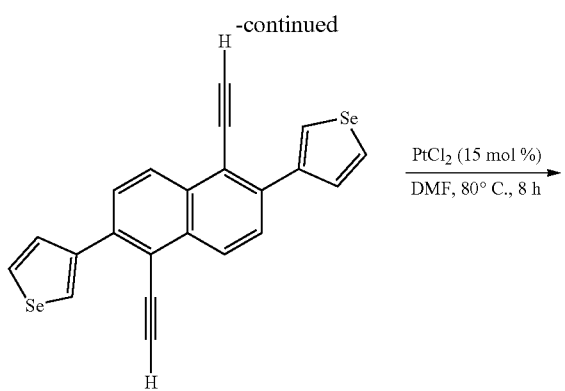

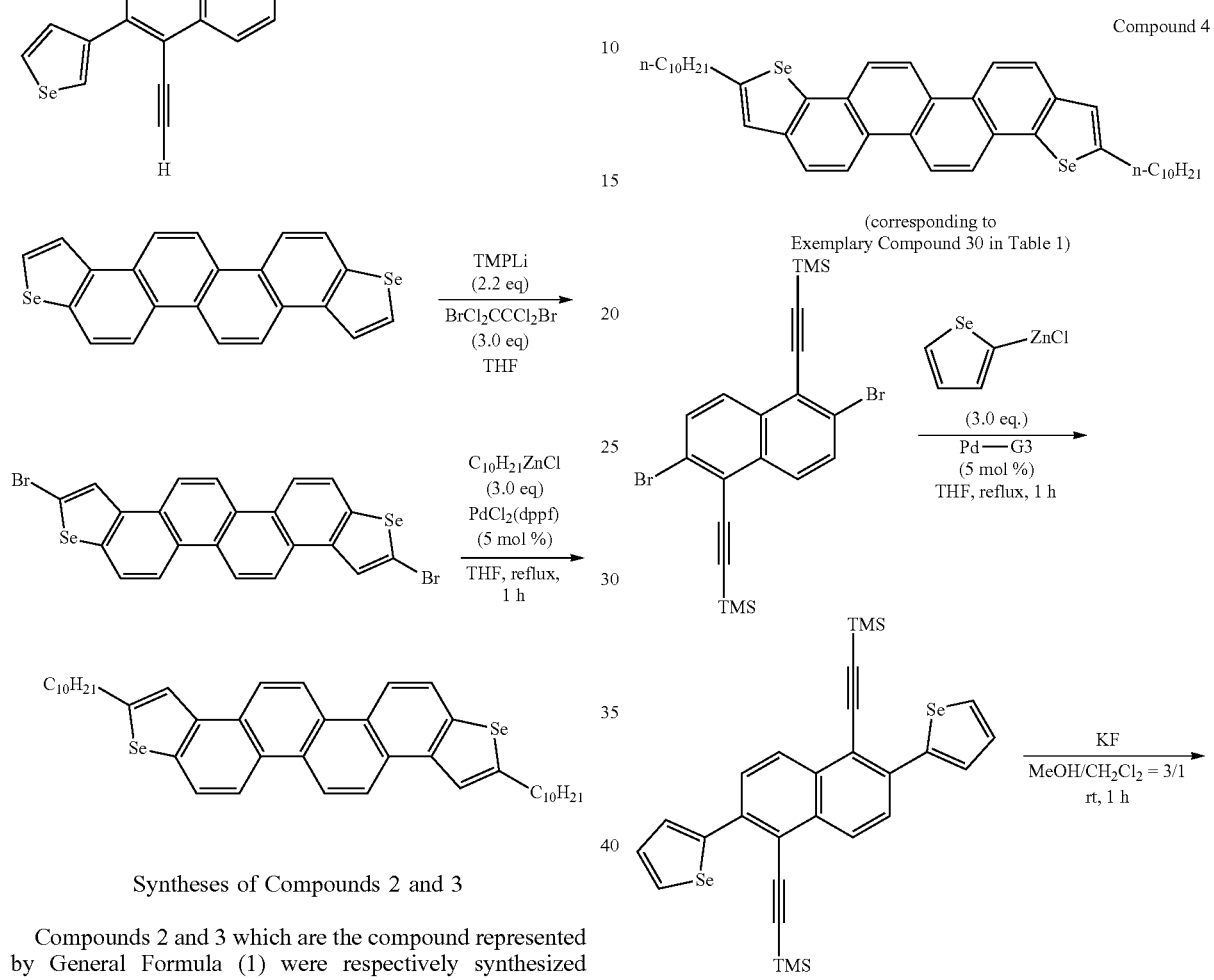

Synthesis of Compound 4

A compound 4 (corresponding to Exemplary Compound 30 in Table 1) which is the compound represented by General Formula (1) was synthesized according to a specific synthesis order illustrated in the following scheme.

Syntheses of Compounds 2 and 3

Compounds 2 and 3 which are the compound represented by General Formula (1) were respectively synthesized according to the synthesis method of the compound 1.

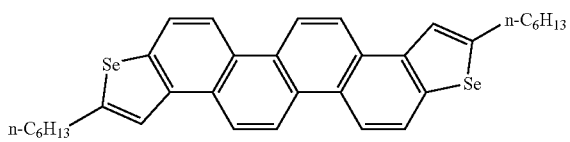

(corresponding to Exemplary Compound 2 in Table 1)

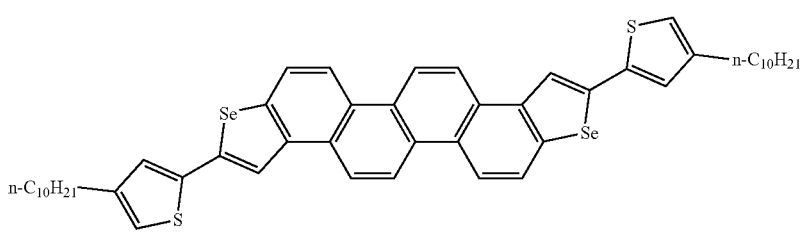

(corresponding to Exemplary Compound 6 in Table 1)

-continued

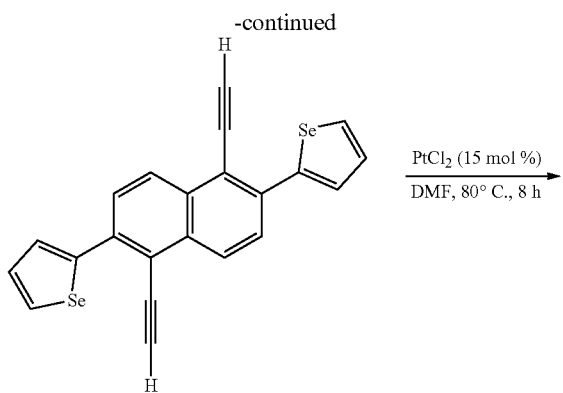

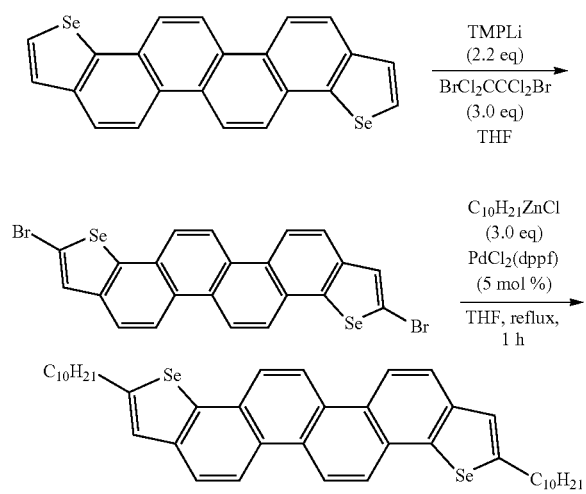

Synthesis of Compound 5

A compound 5 which is the compound represented by General Formula (1) was synthesized according to the synthesis method of the compound 4.

Compound 5

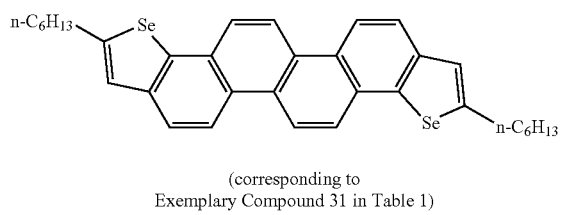

(corresponding to Exemplary Compound 31 in Table 1)

Syntheses of Comparative Compounds 1 to 3

Comparative compounds 1 to 3 which were to be used for organic semiconductor films (organic semiconductor layers) of comparative elements were synthesized according to the synthesis method described in JP2014-078729A. The structures of the comparative compounds 1 to 3 will be illustrated below.

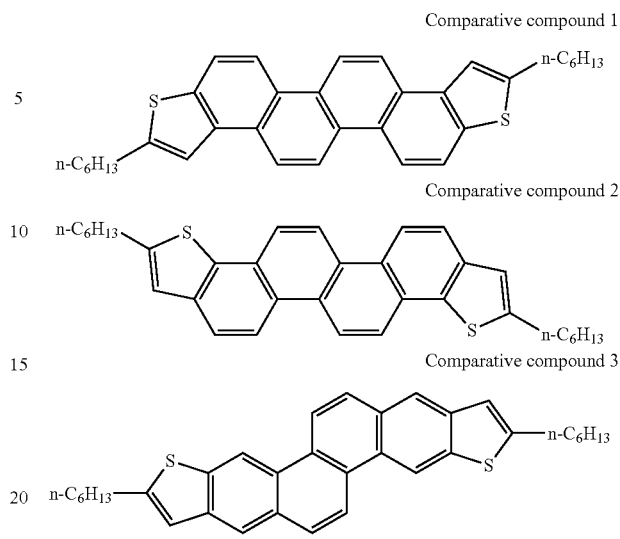

<<Production and Evaluation of Elements>>

For the materials for an organic thin-film transistor used to produce elements (the respective compounds described above), the purities (the absorption intensity area ratio at 254 nm) were confirmed to be 99.0% or higher by means of high-speed liquid chromatography (TSKgel ODS-100Z manufactured by Tosoh Corporation).

<Production of Bottom Gate-Top Contact-Type Element by Coating Process>

The compound 1 synthesized above and anisole as a solvent were mixed together so as to prepare 0.05% by mass of a solution, and the solution was heated to 80° C., thereby producing a composition for an organic thin-film transistor 1.

In addition, compositions for an organic thin-film transistor 2 to 5 and compositions for an organic thin-film transistor for comparison 1 to 3 were respectively prepared using the same method except for the fact that any one of the compounds 2 to 5 and the comparative compounds 1, 2, and 3 was used instead of the compound 1.

Figure 3:
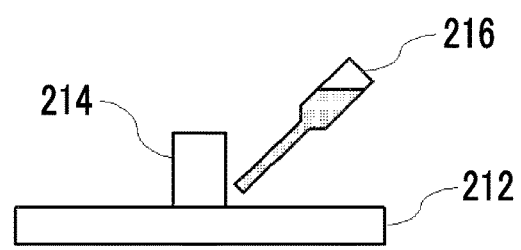
FIG. 3 is a schematic view illustrating a step of a method for manufacturing an organic semiconductor film in examples and comparative examples.
Figure 4A:
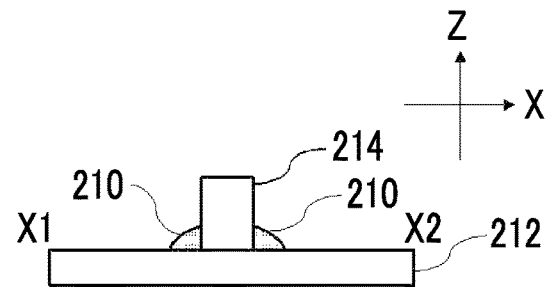
FIG. 4A is a schematic view illustrating a step of the method for manufacturing an organic semiconductor film in the examples and the comparative examples.
Figure 4B:
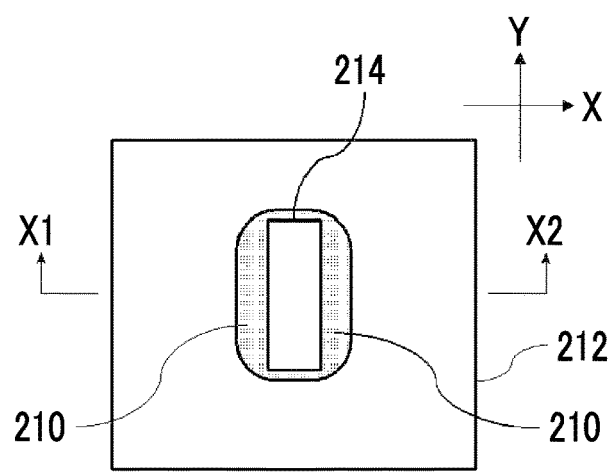
FIG. 4B is a schematic view illustrating a step of the method for manufacturing an organic semiconductor film in the examples and the comparative examples.
Figure 5:
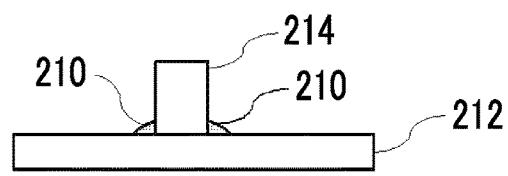
FIG. 5 is a schematic view illustrating a step of the method for manufacturing an organic semiconductor film in the examples and the comparative examples.

In the example and the comparative examples, organic semiconductor films were formed using the method illustrated in FIG. 3 to FIG. 5. FIG. 3 to FIG. 5 are schematic views illustrating a method for manufacturing the organic semiconductor films of the examples and the comparative examples.

The method for forming the organic semiconductor film will be described in detail using a case in which the composition for an organic thin-film transistor 1 was used as an example.

A 10 mm×10 mm substrate obtained by forming a 500 nm-thick $SiO_2$ thermally oxidized film on the surface of an n-type silicon substrate (thickness: 0.4 mm) was used as a substrate 212. The thermally oxidized film-side surface of the substrate 212 was washed with ultraviolet (UV)-ozone and then subjected to a β-phenethyltrimethoxysilane treatment.

On the β-phenethyltrimethoxysilane-treated surface of the substrate 212, a member 214 was placed in the central portion of the substrate 212 as illustrated in FIG. 3 so as to come into contact with the substrate 212. As the member 214, a glass member having a length of 6 mm, a width of 1 mm, and a height of 2 mm was used. The horizontal direction (X-axis direction) in FIG. 3 is the width direction of the member 214, the vertical direction (Z-axis direction) in FIG. 3 is the height direction of the member 214, and the vertical direction (Y-axis direction) in FIG. 4B is the length direction of the member 214.

The substrate 212 was heated to 70° C., and one droplet (approximately 0.03 ml) of the composition for an organic thin-film transistor 1 (a composition for an organic thin-film transistor 210 illustrated in FIGS. 3 to 5) prepared using the above-described method was dropped on the substrate using a pipette 216 through a side portion of the member 214 so as to come into contact with both the substrate 212 and the member 214 as illustrated in FIG. 3, thereby adding the composition for an organic thin-film transistor 1 dropwise to a portion on the surface of the substrate 212 as illustrated in FIG. 4A and FIG. 4B. A concave meniscus was formed in the interface with the member 214.

The dropwise-added composition for an organic thin-film transistor 1 was naturally dried in a state in which the substrate 212 and the member 214 were in contact with each other and the positional relationship between the substrate 212 and the member 214 was fixed as illustrated in FIG. 5. After that, the composition was dried at a reduced pressure of $10^{-3}$ MPa and 60° C. for eight hours so as to precipitate the crystals of Compound 1, thereby forming an organic semiconductor film. Whether or not crystals were precipitated was checked by means of observation using a polarization microscope. Meanwhile, the film thickness of the obtained organic semiconductor film was 70 nm.

Furthermore, a mask was worn on the obtained organic semiconductor film, and a 2 nm-thick 2,3,5,6-tetrafluoro-7,7,8,8-tetracyanoquinodimethan (F4-TCNQ) as a charge injection acceptor and a 40 nm-thick metal electrode were respectively deposited thereon, thereby obtaining an organic thin-film transistor element 1 for measuring field-effect transistor (FET) characteristics (hereinafter, also referred to as "element 1").

In addition, organic thin-film transistor elements 2 to 5 (hereinafter, also referred to as "elements 2 to 5") and comparative organic thin-film transistor elements 1 to 3 (hereinafter, also referred to as "comparative elements 1 to 3") were respectively produced according to the method for producing the element 1 except for the fact that any one of the compositions for an organic thin-film transistor 2 to 5 and the compositions for an organic thin-film transistor for comparison 1, 2, and 3 was used instead of the composition for an organic thin-film transistor 1. The obtained elements 1 to 5 and the comparative elements 1 to 3 were considered as organic thin-film transistors of Examples 1 to 5 and Comparative Examples 1 to 3.

<Evaluation>

The FET characteristics of each of the organic thin-film transistor elements (the elements 1 to 5 and the comparative elements 1 to 3) were evaluated from the viewpoint of carrier mobility at normal pressure in the atmosphere using a semiconductor parameter analyzer (manufactured by Agilent, 4156C) to which a semi-auto prober (manufactured by Vector Semiconductor Co., Ltd., AX-2000) was connected.

(Carrier Mobility)

A voltage of −50 V was applied between a source electrode and a drain electrode in each of the organic thin-film transistor element (FET element), the gate voltage was changed in a range of 20 V to −150 V, and the carrier mobility μ was computed using an expression expressing the drain current $I_d = (w/2L)\mu C_i(V_g - V_{th})^2$ (in the expression, L represents the gate length, W represents the gate width, $C_i$ represents the capacity of an insulating layer per unit area, $V_g$ represents the gate voltage, and $V_{th}$ represents the threshold voltage) and evaluated using the following four levels.

The obtained results are shown in the following table.

"A": ≥2 cm²/Vs
"B": 1 cm²/Vs or more to less than 2 cm²//Vs
"C": 0.1 cm²/Vs or more to less than 1 cm²//Vs
"D": <0.1 cm²/Vs

TABLE 25

| | Element No. | Material for organic thin-film transistor | Carrier mobility (cm²/Vs) |
| --- | --- | --- | --- |
| Example 1 | Element 1 | Compound 1 | A |
| Example 2 | Element 2 | Compound 2 | A |
| Example 3 | Element 3 | Compound 3 | A |
| Example 4 | Element 4 | Compound 4 | A |
| Example 5 | Element 5 | Compound 5 | A |
| Comparative Example 1 | Comparative element 1 | Comparative compound 1 | C |
| Comparative Example 2 | Comparative element 2 | Comparative compound 2 | C |
| Comparative Example 3 | Comparative element 3 | Comparative compound 3 | D |

Examples 6 to 10 and Comparative Examples 4 to 6

<<Production and Evaluation of Elements>>
<Production of Bottom Gate-Bottom Contact-Type Element by Coating Process>

In Examples 6 to 10 and Comparative Examples 4 to 6, bottom gate-bottom contact-type organic thin-film transistor elements were produced. The details will be described below.

The composition for an organic thin-film transistor 1 obtained by heating the anisole solution of 0.05% by mass of the compound 1 to 80° C. in Example 1 was cast (using a drop casting method) onto a substrate for measuring FET characteristics heated to 70° C., which will be described below, in a nitrogen atmosphere, thereby obtaining a non-luminous organic thin-film transistor element 6 (hereinafter, also referred to as "element 6").

As the substrate for measuring FET characteristics, a bottom gate and bottom contact-structured silicon substrate including chromium/gold disposed in a comb shape (gate width W: 100 mm, gate length L: 100 μm) as source and drain electrodes and SiO₂ (film thickness: 500 nm) as an insulating film was used.

Organic thin-film transistor elements 7 to 10 (hereinafter, also referred to as "elements 7 to 10") and comparative organic thin-film transistor elements 4 to 6 (hereinafter, also referred to as "comparative elements 4 to 6") were respectively produced according to the method for producing the element 6 except for the fact that any one of the compositions for an organic thin-film transistor 2 to 5 and the compositions for an organic thin-film transistor for comparison 1, 2, and 3 was used instead of the composition for an organic thin-film transistor 1. The obtained elements 6 to 10 and the comparative elements 4 to 6 were considered as organic thin-film transistors of Examples 6 to 10 and Comparative Examples 4 to 6.

<Evaluation>

The FET characteristics of each of the organic thin-film transistor elements (the elements 6 to 10 and the comparative elements 4 to 6) were evaluated using the same method as in Example 1. The results are shown in the following table.

TABLE 26

| Element No. | Material for organic thin-film transistor | Carrier mobility (cm²/Vs) |
|---|---|---|---|
| Example 6 | Element 6 | Compound 1 | A |
| Example 7 | Element 7 | Compound 2 | A |
| Example 8 | Element 8 | Compound 3 | A |
| Example 9 | Element 9 | Compound 4 | B |
| Example 10 | Element 10 | Compound 5 | B |
| Comparative Example 4 | Comparative element 4 | Comparative compound 1 | D |
| Comparative Example 5 | Comparative element 5 | Comparative compound 2 | D |
| Comparative Example 6 | Comparative element 6 | Comparative compound 3 | D |

Examples 11 to 14 and Comparative Examples 7 to 9

<Production of Bottom Gate-Top Contact-Type Element by Deposition Process>

The oxidized film-side surface of the substrate 212 was washed with UV-ozone using the same method as in Example 1 and then subjected to a dodecyltrichlorosilane treatment.

On the dodecyltrichlorosilane-treated surface of the substrate 212, a film of the compound 1 was deposited and grown at a deposition rate of 0.05 nm/s so as to obtain a film thickness of 40 nm.

Furthermore, a mask was worn on the obtained organic semiconductor film, and a 2 nm-thick F4-TCNQ as a charge injection acceptor and a 40 nm-thick metal electrode were respectively deposited thereon, thereby obtaining an organic thin-film transistor element 11 for measuring FET characteristics (hereinafter, also referred to as "element 11").

Organic thin-film transistor elements 12 to 14 (hereinafter, also referred to as "elements 12 to 14") and comparative organic thin-film transistor elements 7 to 9 (hereinafter, also referred to as "comparative elements 7 to 9") were respectively produced using the same method as for the element 11 except for the fact that any one of the compounds 2, 4, and 5 and the comparative compounds 1, 2, and 3 was used instead of the compound 1. The obtained elements 11 to 14 and the comparative elements 7 to 9 were considered as organic thin-film transistors of Examples 11 to 14 and Comparative Examples 7 to 9.

<Evaluation>

The FET characteristics of each of the organic thin-film transistor elements (the elements 11 to 14 and the comparative elements 7 to 9) were evaluated using the same method as in Example 1. The results are shown in the following table.

TABLE 27

| Element No. | Material for organic thin-film transistor | Carrier mobility (cm²/Vs) |
|---|---|---|---|
| Example 11 | Element 11 | Compound 1 | A |
| Example 12 | Element 12 | Compound 2 | A |
| Example 13 | Element 13 | Compound 3 | A |
| Example 14 | Element 14 | Compound 4 | B |

TABLE 27-continued

| Element No. | Material for organic thin-film transistor | Carrier mobility (cm²/Vs) |
|---|---|---|---|
| Comparative Example 7 | Comparative element 7 | Comparative compound 1 | C |
| Comparative Example 8 | Comparative element 8 | Comparative compound 2 | C |
| Comparative Example 9 | Comparative element 9 | Comparative compound 3 | D |

From the above-described evaluation results, it was confirmed that, in the organic thin-film transistor elements of the respective examples (Examples 1 to 14) for which the compound represented by General Formula (1) was used, the carrier mobility was high, and it was clarified that the compound represented by General Formula (1) can be preferably used as a material for an organic thin-film transistor.

In addition, from the respective comparison between the examples in which the compounds 1 to 3 that are structural isomers in which only the location of the selenium atom was different in selenophene which is a heteroaromatic ring of a 5-membered ring corresponding to Z in General Formula (1) were used and the examples in which the compounds 4 and 5 were used (refer to Tables 2 to 4), it was found that the examples in which the compounds 1 to 3 (compounds corresponding to General Formula (1X)) were used imparted an excellent carrier mobility in any forms regardless of film-forming means such as coating or deposition and the transistor layer constitutions.

In addition, from the comparison among the respective examples in which the compounds 1 to 5 were used (refer to Tables 2 and 4), it was found that, in a case in which the edge casting method carried out in Example 1 was used as the film-forming means for the compound represented by General Formula (1), a more favorable carrier mobility could be obtained.

In addition, from the comparison between Example 13 in which the compound 4 in which, in selenophene which is a heteroaromatic ring of a 5-membered ring corresponding to Z in General Formula (1), the location of the selenium atom was the same and only the kind of the substituent was different was used and Example 14 in which the compound 5 was used (refer to Table 4), it was found that, in the case of having an aliphatic hydrocarbon group (preferably having 4 to 12 carbon atoms and more preferably having 8 to 12 carbon atoms) of a longer chain, a more favorable carrier mobility could be obtained.

Meanwhile, it was clarified that, in all of the organic thin-film transistor elements in which the comparative compounds 1 to 3 that are not in the scope of General Formula (1) were used for the organic semiconductor layers as the materials for an organic thin-film transistor (Comparative Examples 1 to 9), the carrier mobility was low.

Examples 15 to 19 and Comparative Examples 10 to 12

<Production of Bottom Gate-Bottom Contact-Type Element Using Polymer Binder>

Bottom gate-bottom contact-type elements 15 were produced in the same manner as in Example 6 except for the fact that a material containing the compound 1 and poly α-methylstyrene in a mass ratio of 1:1 (material 1') was used instead of the compound 1 in Example 6. Organic thin-film transistor elements 16 to 19 (hereinafter, also referred to as "elements 16 to 19") and comparative organic thin-film transistor elements 10 to 12 (hereinafter, also referred to as "comparative elements 10 to 12") were respectively produced using the same method except for the fact that, in the production of the elements 15, any one of the compounds 2 to 5 and the comparative compounds 1, 2, and 3 was used instead of the compound 1. The obtained elements 15 to 19 and the comparative elements 10 to 12 were considered as organic thin-film transistors of Examples 15 to 19 and Comparative Examples 10 to 12.

<Evaluation>

The FET characteristics of each of the organic thin-film transistor elements (the elements 15 to 19 and the comparative elements 10 to 12) were evaluated using the same method as in Example 1. The results are shown in the following table.

TABLE 28

| | Element No. | Material for organic thin-film transistor | Carrier mobility ($cm^2/Vs$) |
|---|---|---|---|
| Example 15 | Element 15 | Material 1' | A |
| Example 16 | Element 16 | Material 2' | A |
| Example 17 | Element 17 | Material 3' | A |
| Example 18 | Element 18 | Material 4' | B |
| Example 19 | Element 19 | Material 5' | B |
| Comparative Example 10 | Comparative element 10 | Comparative material 1' | D |
| Comparative Example 11 | Comparative element 11 | Comparative material 2' | D |
| Comparative Example 12 | Comparative element 12 | Comparative material 3' | D |

From the table, it was confirmed that, in the organic thin-film transistor elements of the respective examples for which the compound represented by General Formula (1) of the present invention was used, the carrier mobility was high even in the case of the bottom gate-bottom contact-type elements and the case of using the polymer binders, and it was found that the compound represented by General Formula (1) of the present invention can be preferably used as organic thin-film transistor materials.

Meanwhile, it was found that the organic thin-film transistor elements in which the comparative compounds 1, 2, and 3 that are not in the scope of General Formula (1) were used for the organic semiconductor layers as the organic thin-film transistor material, the carrier mobility was low.

Examples 20 to 24

<<Production and Evaluation of Elements>>
<Production of Bottom Gate-Bottom Contact-Type Element by Printing Method>
—Ink Jet Method—

The compound 1 and tetralin as a solvent were mixed together so as to prepare 0.1% by mass of a solution, and the solution was considered as a composition for an organic thin-film transistor 20. In addition, compositions for an organic thin-film transistor 21 to 24 were prepared in the same manner except for the fact that the respective compounds 2 to 5 were used instead of the compound 1.

An organic semiconductor film was formed on the same bottom gate-bottom contact-type substrate for measuring FET characteristics as in Example 6 using the composition for an organic thin-film transistor 20 and an ink jet method, thereby obtaining a non-luminous organic thin-film transistor element 20 (hereinafter, also referred to as "element 20").

Meanwhile, the specific method for producing the organic semiconductor film using the ink jet method is as described below.

As an ink jet apparatus, a 10 pl head of DMP2831 (manufactured by Fuji Graphic Systems) was used, and a beta film was formed at a jetting frequency of 2 Hz and an inter-dot pitch of 20 μm. After that, the beta film was dried at 70° C. for one hour, thereby forming an organic semiconductor film.

Organic thin-film transistor elements 21 to 24 (hereinafter, also referred to as "elements 21 to 24") were respectively produced according to the method for producing the element 20 except for the fact that the compositions for an organic thin-film transistor 21 to 24 were used instead of the composition for an organic thin-film transistor 20. The obtained elements 20 to 24 were considered as organic thin-film transistors of Examples 20 to 24.

<Evaluation>

The FET characteristics of each of the organic thin-film transistor elements (the elements 20 to 24) were evaluated using the same method as in Example 1. The results are shown in the following table.

TABLE 29

| | Element No. | Material for organic thin-film transistor | Carrier mobility ($cm^2/Vs$) |
|---|---|---|---|
| Example 20 | Element 20 | Compound 1 | A |
| Example 21 | Element 21 | Compound 2 | A |
| Example 22 | Element 22 | Compound 3 | A |
| Example 23 | Element 23 | Compound 4 | B |
| Example 24 | Element 24 | Compound 5 | B |

As shown in Table 6, it was confirmed that, in all of the organic thin-film transistor elements of the respective examples including the organic semiconductor layers obtained by forming a film of the compound represented by General Formula (1) of the present invention using the ink jet method, the carrier mobility was high and it was found that the compound represented by General Formula (1) of the present invention can be preferably used as organic thin-film transistor materials.

Examples 25 to 29

<Production of Inverter>

Figure 6:
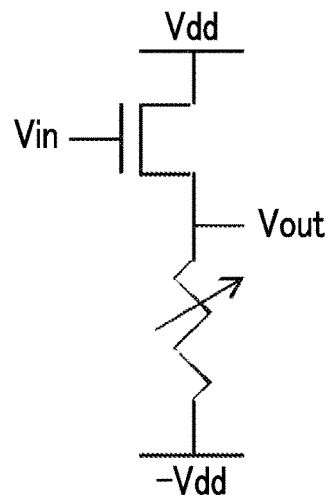
FIG. 6 is a schematic view of an inverter produced in the examples.

A variable resistance was connected to the organic thin-film transistor element of Example 1 as illustrated in FIG. 6, and the resistance value of the variable resistance was set to an appropriate value, thereby producing an inverter element 25. In addition, inverter elements 26 to 29 were produced using the organic thin-film transistor elements of Example 2 to Example 5 instead of the organic thin-film transistor element of Example 1. All of the inverter elements exhibited favorable inverter characteristics of 10 or higher gains.

Examples 30 to 34

<Production of Ring Oscillator>

Figure 7:
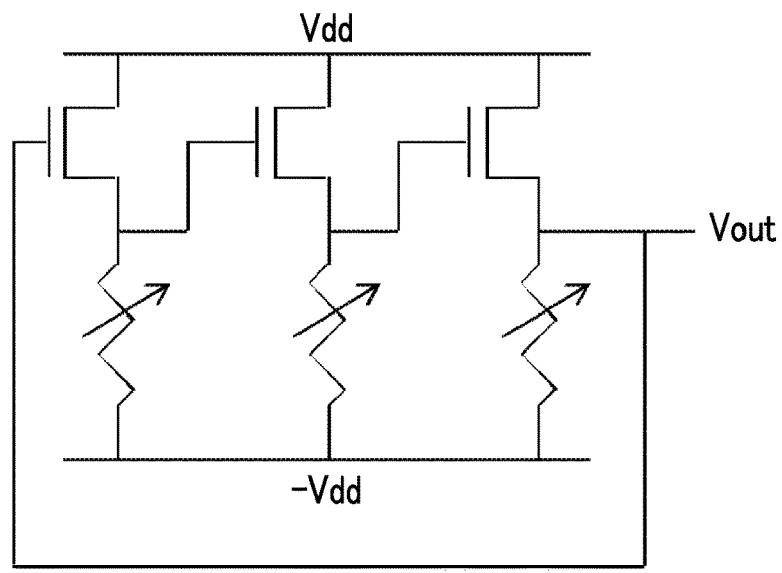
FIG. 7 is a schematic view of a ring oscillator produced in the examples.

The inverter elements of Example 25 were linked in three levels as illustrated in FIG. 7, thereby producing a ring oscillator element 30. In addition, ring oscillator elements 31 to 34 were produced using the inverter elements of Example 26 to Example 29 instead of the ring oscillator element of Example 25. All of the ring oscillator elements stably generated oscillations.

As described above, it has been shown that a variety of kinds of devices can be produced using the compound of the present invention.

EXPLANATION OF REFERENCES

10: substrate, 20: gate electrode, 30: gate insulating film, 40: source electrode, 42: drain electrode, 50: organic semiconductor film (organic semiconductor layer), 60: sealing layer, 100, 200: organic thin-film transistor, 210: composition for organic thin-film transistor, 212: substrate, 214: member, 216: pipette

What is claimed is:

1. An organic thin-film transistor comprising:
    an organic semiconductor film including a compound which is represented by General Formula (1) and has a molecular weight of 3,000 or less, General Formula (1)

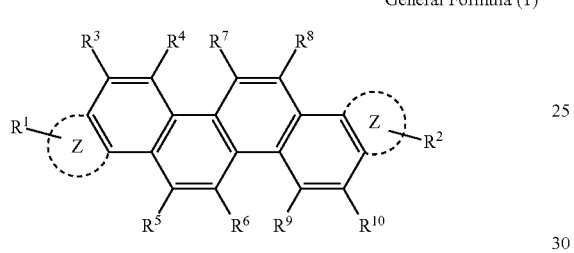

Z represents a heteroaromatic ring of a 5-membered ring selected from the group consisting of selenophene, thiazole, oxazole, imidazole, and silole, $R^1$ to $R^{10}$ each independently represent a group represented by Formula (W), $$-L^W-R^W \qquad (W)$$

in Formula (W), $L^W$ is a divalent linking group of any of a single bond, —O—, —S—, —NR$^{11}$—, —CO—, —SO—, —SO$_2$—, or —Si(R$^{12}$)(R$^{13}$) or a divalent linking group obtained by bonding two or more divalent linking groups described above, $R^W$ represents a hydrogen atom, a halogen atom, or an alkyl group, an alkenyl group, an alkynyl group, an aryl group, or a heteroaryl group, all of which may have a substituent, and
    $R^{11}$ to $R^{13}$ each independently represent a hydrogen atom or an alkyl group, an alkenyl group, an alkynyl group, an aryl group, or a heteroaryl group, all of which may have a substituent.

2. The organic thin-film transistor according to claim 1, wherein, in General Formula (1), the number of carbon atoms included in each of $R^1$ to $R^{10}$ is independently 30 or less.

3. The organic thin-film transistor according to claim 1, wherein, in General Formula (1), at least one of $R^1, \ldots,$ or $R^{10}$ has, as $R^W$, any group selected from the group consisting of an alkyl group having 20 or less carbon atoms, an aryl group having 20 or less carbon atoms, and a heteroaryl group having 20 or less carbon atoms, all of which may have a substituent.

4. The organic thin-film transistor according to claim 1, wherein, in General Formula (1), $R^1$ and $R^2$ are the same group, $R^3$ and $R^{10}$ are the same group, $R^4$ and $R^9$ are the same group, $R^5$ and $R^8$ are the same group, and $R^6$ and $R^7$ are the same group.

5. The organic thin-film transistor according to claim 1, wherein the compound is represented by General Formula (2) or General Formula (3), General Formula (2)

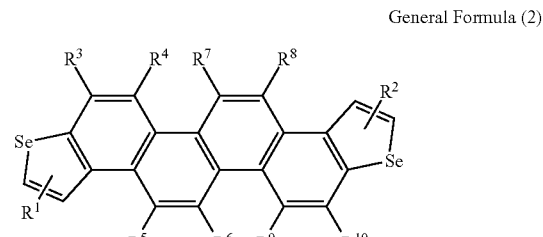

General Formula (3)

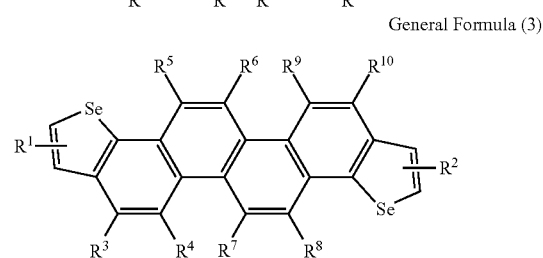

$R^1$ to $R^{10}$ each independently represent a group represented by Formula (W), $$-L^W-R^W \qquad (W)$$

in Formula (W), $L^W$ is a divalent linking group of any of a single bond, —O—, —S—, —NR$^{11}$—, —CO—, —SO—, —SO$_2$—, or —Si(R$^{12}$)(R$^{13}$) or a divalent linking group obtained by bonding two or more divalent linking groups described above, $R^W$ represents a hydrogen atom, a halogen atom, or an alkyl group, an alkenyl group, an alkynyl group, an aryl group, or a heteroaryl group, all of which may have a substituent,
    $R^{11}$ to $R^{13}$ each independently represent a hydrogen atom or an alkyl group, an alkenyl group, an alkynyl group, an aryl group, or a heteroaryl group, all of which may have a substituent,
    here, at least one of $R^1, \ldots,$ or $R^{10}$ has, as $R^W$, any group selected from the group consisting of an alkyl group having 20 or less carbon atoms, an aryl group having 20 or less carbon atoms, and a heteroaryl group having 20 or less carbon atoms, all of which may have a substituent, and
    $R^1$ and $R^2$ are the same group, $R^3$ and $R^{10}$ are the same group, $R^4$ and $R^9$ are the same group, $R^5$ and $R^8$ are the same group, and $R^6$ and $R^7$ are the same group.

6. The organic thin-film transistor according to claim 1, wherein the compound is represented by General Formula (4) or General Formula (5), General Formula (4)

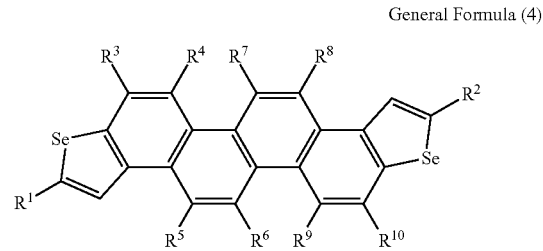

General Formula (5)

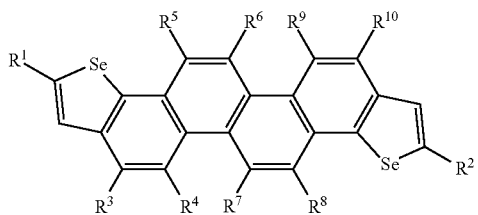

in General Formulae (4) and (5), $R^1$ to $R^{10}$ each independently represent a group represented by Formula (W), $$-L^W-R^W \qquad (W)$$

in Formula (W), $L^W$ is a divalent linking group of any of a single bond, —O—, —S—, —NR$^{11}$—, —CO—, —SO—, —SO$_2$—, or —Si(R$^{12}$)(R$^{13}$) or a divalent linking group obtained by bonding two or more divalent linking groups described above, $R^W$ represents a hydrogen atom, a halogen atom, or an alkyl group, an alkenyl group, an alkynyl group, an aryl group, or a heteroaryl group, all of which may have a substituent, $R^{11}$ to $R^{13}$ each independently represent a hydrogen atom or an alkyl group, an alkenyl group, an alkynyl group, an aryl group, or a heteroaryl group, all of which may have a substituent, here, at least one of $R^1, \ldots,$ or $R^{10}$ has, as $R^W$, any group selected from the group consisting of an alkyl group having 20 or less carbon atoms, an aryl group having 20 or less carbon atoms, and a heteroaryl group having 20 or less carbon atoms, all of which may have a substituent, and $R^1$ and $R^2$ are the same group, $R^3$ and $R^{10}$ are the same group, $R^4$ and $R^9$ are the same group, $R^5$ and $R^8$ are the same group, and $R^6$ and $R^7$ are the same group.

7. The organic thin-film transistor according to claim 1, wherein the compound is represented by General Formula (6) or General Formula (7), General Formula (6)

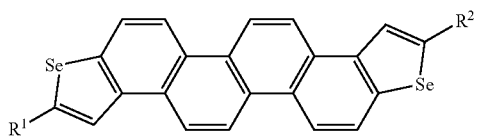

General Formula (7)

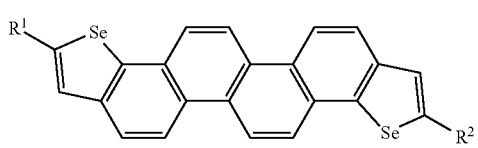

in General Formulae (6) and (7), $R^1$ and $R^2$ are the same group and each represent a group represented by Formula (W), $$-L^W-R^W \qquad (W)$$

in Formula (W), $L^W$ is a divalent linking group of any of a single bond, —O—, —S—, —NR$^{11}$—, —CO—, —SO—, —SO$_2$—, or —Si(R$^{12}$)(R$^{13}$) or a divalent linking group obtained by bonding two or more divalent linking groups described above, $R^W$ represents an alkyl group having 20 or less carbon atoms, an aryl group having 20 or less carbon atoms, or a heteroaryl group having 20 or less carbon atoms, all of which may have a substituent, and $R^{11}$ to $R^{13}$ each independently represent a hydrogen atom or an alkyl group, an alkenyl group, an alkynyl group, an aryl group, or a heteroaryl group, all of which may have a substituent.

8. The organic thin-film transistor according to claim 7, wherein, in General Formula (6) or (7), $L^W$ is a single bond.

9. The organic thin-film transistor according to claim 7, wherein, in General Formula (6) or (7), both $R^1$ and $R^2$ include an aliphatic hydrocarbon group having 20 or less carbon atoms.

10. A compound which is represented by General Formula (1) and has a molecular weight of 3,000 or less, General Formula (1)

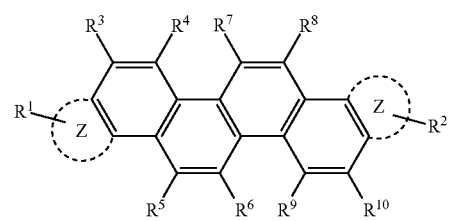

Z represents a heteroaromatic ring of a 5-membered ring selected from the group consisting of selenophene, thiazole, oxazole, imidazole, and silole, $R^1$ to $R^{10}$ each independently represent a group represented by Formula (W), $$-L^W-R^W \qquad (W)$$

in Formula (W), $L^W$ is a divalent linking group of any of a single bond, —O—, —S—, —NR$^{11}$—, —CO—, —SO—, —SO$_2$—, or —Si(R$^{12}$)(R$^{13}$) or a divalent linking group obtained by bonding two or more divalent linking groups described above, $R^W$ represents a hydrogen atom, a halogen atom, or an alkyl group, an alkenyl group, an alkynyl group, an aryl group, or a heteroaryl group, all of which may have a substituent, and $R^{11}$ to $R^{13}$ each independently represent a hydrogen atom or an alkyl group, an alkenyl group, an alkynyl group, an aryl group, or a heteroaryl group, all of which may have a substituent.

11. The compound according to claim 10, wherein, in General Formula (1), the number of carbon atoms included in each of $R^1$ to $R^{10}$ is independently 30 or less.

12. The compound according to claim 10, wherein, in General Formula (1), at least one of $R^1, \ldots,$ or $R^{10}$ has, as $R^W$, any group selected from the group consisting of an alkyl group having 20 or less carbon atoms, an aryl group having 20 or less carbon atoms, and a heteroaryl group having 20 or less carbon atoms, all of which may have a substituent.

13. The compound according to claim 10, wherein, in General Formula (1), $R^1$ and $R^2$ are the same group, $R^3$ and $R^{10}$ are the same group, $R^4$ and $R^9$ are the same group, $R^5$ and $R^8$ are the same group, and $R^6$ and $R^7$ are the same group.

14. The compound according to claim 10,
wherein the compound is represented by General Formula (2) or General Formula (3), General Formula (2)

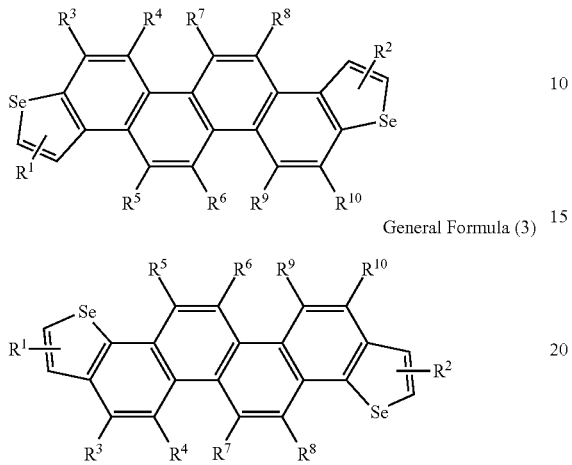

General Formula (3)

in General Formulae (2) and (3), $R^1$ to $R^{10}$ each independently represent a group represented by Formula (W),

-L$^W$-R$^W$     (W)

in Formula (W), L$^W$ is a divalent linking group of any of a single bond, —O—, —S—, —NR$^{11}$—, —CO—, —SO—, —SO$_2$—, or —Si(R$^{12}$)(R$^{13}$)— or a divalent linking group obtained by bonding two or more divalent linking groups described above, R$^W$ represents a hydrogen atom, a halogen atom, or an alkyl group, an alkenyl group, an alkynyl group, an aryl group, or a heteroaryl group, all of which may have a substituent, $R^{11}$ to $R^{13}$ each independently represent a hydrogen atom or an alkyl group, an alkenyl group, an alkynyl group, an aryl group, or a heteroaryl group, all of which may have a substituent, here, at least one of $R^1$, . . . , or $R^{10}$ has, as R$^W$, any group selected from the group consisting of an alkyl group having 20 or less carbon atoms, an aryl group having 20 or less carbon atoms, and a heteroaryl group having 20 or less carbon atoms, all of which may have a substituent, and $R^1$ and $R^2$ are the same group, $R^3$ and $R^{10}$ are the same group, $R^4$ and $R^9$ are the same group, $R^5$ and $R^8$ are the same group, and $R^6$ and $R^7$ are the same group.

15. The compound according to claim 10,
wherein the compound is represented by General Formula (4) or General Formula (5), General Formula (4)

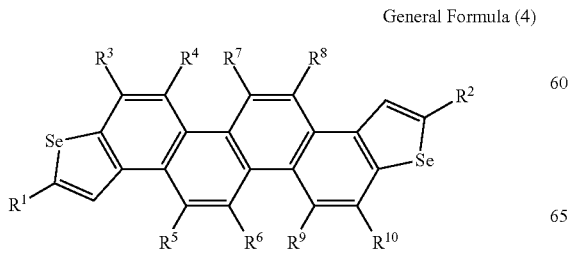

General Formula (5)

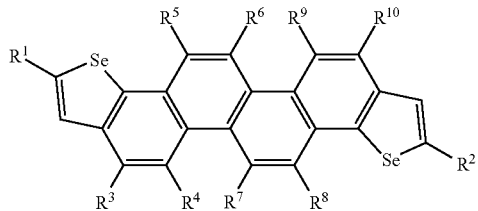

in General Formulae (4) and (5), $R^1$ to $R^{10}$ each independently represent a group represented by Formula (W),

-L$^W$-R$^W$     (W)

in Formula (W), L$^W$ is a divalent linking group of any of a single bond, —O—, —S—, —NR$^{11}$—, —CO—, —SO—, —SO$_2$—, or —Si(R$^{12}$)(R$^{13}$)— or a divalent linking group obtained by bonding two or more divalent linking groups described above, R$^W$ represents a hydrogen atom, a halogen atom, or an alkyl group, an alkenyl group, an alkynyl group, an aryl group, or a heteroaryl group, all of which may have a substituent, $R^{11}$ to $R^{13}$ each independently represent a hydrogen atom or an alkyl group, an alkenyl group, an alkynyl group, an aryl group, or a heteroaryl group, all of which may have a substituent, here, at least one of $R^1$, . . . , or $R^{10}$ has, as R$^W$, any group selected from the group consisting of an alkyl group having 20 or less carbon atoms, an aryl group having 20 or less carbon atoms, and a heteroaryl group having 20 or less carbon atoms, all of which may have a substituent, and $R^1$ and $R^2$ are the same group, $R^3$ and $R^{10}$ are the same group, $R^4$ and $R^9$ are the same group, $R^5$ and $R^8$ are the same group, and $R^6$ and $R^7$ are the same group.

16. The compound according to claim 10,
wherein the compound is represented by General Formula (6) or General Formula (7), General Formula (6)

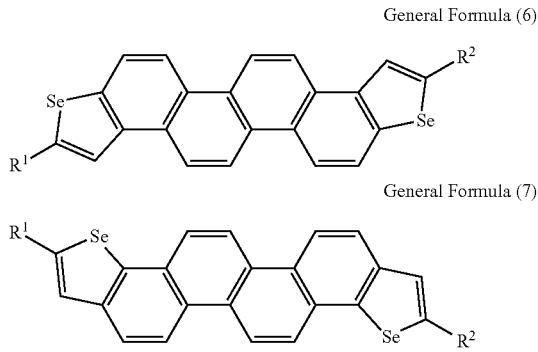

General Formula (7)

in General Formulae (6) and (7), $R^1$ and $R^2$ are the same group and each represent a group represented by Formula (W),

-L$^W$-R$^W$     (W)

in Formula (W), L$^W$ is a divalent linking group of any of a single bond, —O—, —S—, —NR$^{11}$—, —CO—, —SO—, —SO$_2$—, or —Si(R$^2$)(R$^{13}$)— or a divalent linking group obtained by bonding two or more divalent linking groups described above, R$^W$ represents an alkyl group having 20 or less carbon atoms, an aryl group having 20 or less carbon atoms, or a heteroaryl group having 20 or less carbon atoms, all of which may have a substituent, and $R^{11}$ to $R^{13}$ each independently represent a hydrogen atom or an alkyl group, an alkenyl group, an alkynyl group, an aryl group, or a heteroaryl group, all of which may have a substituent.

17. The compound according to claim 16, wherein, in General Formula (6) or (7), $L^W$ is a single bond.

18. The compound according to claim 17, wherein, in General Formula (6) or (7), both $R^1$ and $R^2$ include an aliphatic hydrocarbon group having 20 or less carbon atoms.

19. A material for an organic thin-film transistor comprising:
    the compound according to claim 10.

20. A composition for an organic thin-film transistor comprising:
    the compound according to claim 10.

21. A method for manufacturing an organic thin-film transistor comprising:
    a step of forming an organic semiconductor film by applying the composition for an organic thin-film transistor according to claim 20 on a substrate and drying the composition.

22. An organic semiconductor film comprising:
    the compound according to claim 10.

* * * * *